(12) United States Patent
Kweon et al.

(10) Patent No.: US 11,741,574 B2
(45) Date of Patent: Aug. 29, 2023

(54) METHOD AND DEVICE FOR PROCESSING BLOOD VESSEL IMAGE ON BASIS OF USER INPUT

(71) Applicant: MEDIPIXEL, INC., Seoul (KR)

(72) Inventors: Jihoon Kweon, Gyeonggi-do (KR); Young-Hak Kim, Seoul (KR); Kyo Seok Song, Seoul (KR); Hwi Kwon, Seoul (KR)

(73) Assignee: MEDIPIXEL, INC., Seoul (KR)

( * ) Notice: Subject to any disclaimer, the term of this patent is extended or adjusted under 35 U.S.C. 154(b) by 0 days.

(21) Appl. No.: 17/924,679

(22) PCT Filed: Apr. 28, 2021

(86) PCT No.: PCT/KR2021/005374
§ 371 (c)(1),
(2) Date: Nov. 10, 2022

(87) PCT Pub. No.: WO2021/246648
PCT Pub. Date: Dec. 9, 2021

(65) Prior Publication Data
US 2023/0186433 A1   Jun. 15, 2023

(30) Foreign Application Priority Data

Jun. 2, 2020   (KR) .................. 10-2020-0066266

(51) Int. Cl.
*G06T 5/00*   (2006.01)
*G06V 10/25*  (2022.01)
(Continued)

(52) U.S. Cl.
CPC .............. *G06T 5/001* (2013.01); *G06T 11/60* (2013.01); *G06V 10/25* (2022.01); *G06V 10/44* (2022.01);
(Continued)

(58) Field of Classification Search
CPC ....... A61B 6/481; A61B 6/504; A61B 6/5217; G06T 2207/20076; G06T 2207/20096;
(Continued)

(56) References Cited

U.S. PATENT DOCUMENTS 10,470,730 B2   11/2019   Benishti et al.
10,524,755 B2   1/2020    Kowarschik et al.
(Continued)

FOREIGN PATENT DOCUMENTS

CN   101551862 A   10/2009
CN   108205807 A   6/2018
(Continued)

OTHER PUBLICATIONS

Office Action issued in KR 10-2020-0066266, dated Jan. 9, 2022, 13 pages.
(Continued)

*Primary Examiner* — Manuchehr Rahmjoo
(74) *Attorney, Agent, or Firm* — MARSHALL, GERSTEIN & BORUN LLP

(57) ABSTRACT

The present disclosure relates to a method, performed by a processor, for processing a blood vessel image from a blood vessel image, the method comprising the steps of: extracting a target blood vessel from a blood vessel image; determining a region of interest (ROI) in an extraction result of the target blood vessel on the basis of a first input received from a user; and within the determined ROI, identifying an error portion in the extraction result on the basis of a second input received from the user, and correcting the identified error portion.

9 Claims, 14 Drawing Sheets

(51) Int. Cl.
*G06V 10/44* (2022.01)
*G06T 11/60* (2006.01)

(52) U.S. Cl.
CPC ............... *G06T 2207/10116* (2013.01); *G06T 2207/20104* (2013.01); *G06T 2207/30101* (2013.01)

(58) Field of Classification Search
CPC ......... G06T 2207/30101; G06T 7/0012; G06T 7/11; G06T 7/12; G06T 7/149; G16H 50/30
See application file for complete search history.

(56) References Cited

U.S. PATENT DOCUMENTS

| | | |
|---|---|---|
| 2012/0050565 A1 | 3/2012 | Imai |
| 2016/0328855 A1 | 11/2016 | Lay et al. |
| 2017/0262733 A1 | 9/2017 | Gulsun et al. |
| 2020/0037973 A1* | 2/2020 | Lavi ...................... G06T 7/0012 |

FOREIGN PATENT DOCUMENTS

| | | |
|---|---|---|
| JP | 2016154730 A | 9/2016 |
| KR | 101094838 B1 | 12/2011 |
| KR | 2016/0143178 A | 12/2016 |
| KR | 101937018 B1 | 1/2019 |
| KR | 2019/0141934 A | 12/2019 |
| KR | 10-2399510 | 5/2022 |

OTHER PUBLICATIONS

Notice of Allowance issued in KR Application No. 10-2020-0066266 dated Apr. 19, 2022, 4 pages.
International Search Report for PCT/KR2021/0053754, dated Aug. 6, 2021.

* cited by examiner

METHOD AND DEVICE FOR PROCESSING BLOOD VESSEL IMAGE ON BASIS OF USER INPUT

TECHNICAL FIELD

The following description relates to a method for processing a blood vessel image.

BACKGROUND ART

Angiography images are widely used to diagnose error portions within blood vessels by observing main blood vessels and perform necessary procedures and measures. Conventionally, image processing engines for automatically identifying main blood vessels from a blood vessel image have been used in order to increase convenience and quantify a diagnosis result. For example, a Caas QCA engine from Pie Medical Imaging B. V. may find and display main blood vessels in the angiography images. On the other hand, the main blood vessels extracted from the engine often show errors, such as blood vessel portions (misidentification) other than the main blood vessels to be extracted, a portion (disconnection) to be disconnected, or the like. Therefore, in clinical practices, an identification result obtained by first extracting the main blood vessels from the engine is not used as it is, but manpower is input to check the angiography image, and the errors are directly corrected by the manpower and then the corrected errors are used and stored.

The above-mentioned background art is possessed or acquired by the inventor in the process of deriving the disclosure of the present application and cannot necessarily be said to be a known technology disclosed to the general public prior to the present application.

DISCLOSURE OF THE INVENTION

Technical Goals

Technical Solutions

According to an aspect of the present disclosure, there is provided a method for processing a blood vessel image from performed by a processor, the method including the steps of: extracting a target blood vessel from a blood vessel image; determining a region of interest (ROI) in an extraction result of the target blood vessel on the basis of a first input received from a user; and identifying an error portion in the extraction result on the basis of a second input received from the user, and correcting the identified error portion within the determined ROI.

In an example embodiment, the determining of the ROI may include determining a shape of the ROI on the basis of points in which the first input is detected.

In an example embodiment, the correcting of the error portion may include correcting the error portion on the basis of the plurality of points of the second input, in response to a case where the second input is detected from the plurality of points within the ROI.

In an example embodiment, the correcting of the error portion on the basis of the plurality of points may include detecting whether there is a discontinuity portion in points through which the second input passes, while a point corresponding to the second input moves along a region extracted as the target blood vessel; and connecting discontinued portions along a movement trajectory of the second input in response to a case where the discontinuity portion is detected.

In an example embodiment, the correcting of the error portion on the basis of the movement trajectory may include determining a blood vessel branch located out of a region corresponding to the movement trajectory of the second input among the blood vessel branches connected with the branch point as a misidentification portion, in response to a case where the point corresponding to the second input moves to a region out of the target blood vessel from the branch point within the region extracted as the target blood vessel; and replacing the blood vessel branch with a blood vessel branch indicated by the second input out of the target blood vessel and correcting the remaining extraction result on the basis of the replaced blood vessel branch.

In an example embodiment, the correcting of the error portion may include identifying the error portion from the extraction result of the target blood vessel in response to the determining of the ROI and correcting the identified error portion; and providing the user with a correction result of the error portion.

In an example embodiment, the providing of the user with the correction result may include providing the user with one or more candidate branches in response to a case where the error portion is a misidentification portion; and replacing a branch corresponding to the error portion with the selected branch in response to a case of receiving a pointing input for one branch among the one or more candidate branches from the user.

In an example embodiment, the providing of the user with the correction result may include connecting a region corresponding to a blood vessel branch corresponding to a start point of a user input and a region corresponding to a blood vessel branch corresponding to an end point of the user input, in response to a case where the user input is detected in a plurality of points with respect to the correction result.

In an example embodiment, the correcting of the error portion may include identifying the error portion on the basis of at least one of blood vessel structure data related to the target blood vessel, curvature information of the target blood vessel, diameter information of the target blood vessel, and brightness information of the target blood vessel, in response to a case where the ROI is determined.

In an example embodiment, the correcting of the error portion may include correcting the error portion on the basis of at least one of blood vessel structure data related to the target blood vessel, curvature information of the target blood vessel, diameter information of the target blood vessel, and brightness information of the target blood vessel, in response to a case where the error portion is identified.

In an example embodiment, the correcting of the error portion may include generating a plurality of new extraction results for the target blood vessel in response to a case where the error portion is identified; and selecting one extraction result indicated by the selection input among the plurality of new extraction results in response to the selection input of the user.

According to another aspect of the present disclosure, there is provided a device for processing the blood vessel image including: an image receiver for receiving a blood vessel image; and a processor for extracting a target blood vessel from a blood vessel image, determining a region of interest (ROI) in an extraction result of the target blood vessel on the basis of a first input received from a user, and identifying an error portion in the extraction result on the basis of a second input received from the user, and correcting the identified error portion within the determined ROI.

Advantageous Effects

The method for processing the blood vessel image performed by the device for processing the blood vessel image according to the example embodiment can extract a target blood vessel corresponding to main blood vessels from the blood vessel image in which the contrast agent is inserted. In addition, the device for processing the blood vessel image can determine a region of interest (ROI) by receiving a user input and identify and correct an error portion on the basis of the input received from the user in the ROI.

BEST MODE FOR CARRYING OUT THE INVENTION

Figure 1:
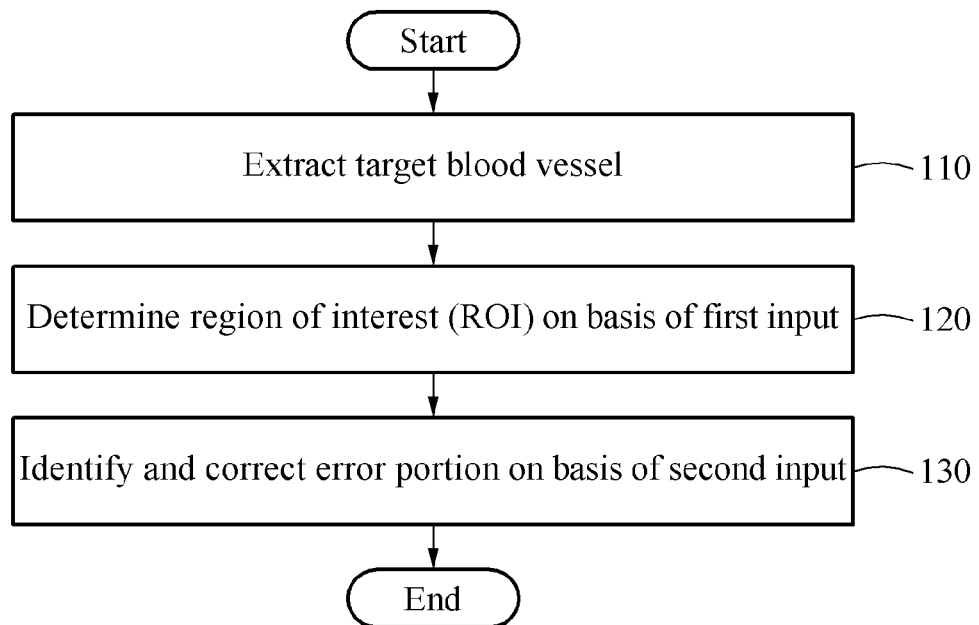
FIG. 1 is a flowchart illustrating a method for processing a blood vessel image according to an example embodiment.

Specific structural or functional descriptions of example embodiments will be disclosed for purposes of only examples, and may be changed and implemented in various forms. Accordingly, the example embodiments are not limited to a specific disclosure form, and the scope of the present specification includes changes, equivalents, or substitutes included in the technical spirit.

Terms such as first or second may be used to describe various components, but these terms should be interpreted only for the purpose of distinguishing one component from other components. For example, a first component may be referred to as a second component, and similarly, the second component may be referred to as the first component.

It should be understood that, when it is described that a component is "connected" to the other component, the component may be directly connected to or access the other component or a third component may be present therebetween.

The singular expression includes the plural expression unless the context clearly dictates otherwise. In the present specification, it should be understood that a term such as "comprise", "have", or the like is intended to designate that a feature, a number, a step, an operation, a component, a part, or a combination thereof described in the specification exists, but it does not preclude the possibility of existence or addition of one or more other features, numbers, steps, operations, components, parts, or combinations thereof.

Unless defined otherwise, all terms used herein, including technical or scientific terms, have the same meaning as those commonly understood by those skilled in the art to which the example embodiments belong. Terms such as those defined in a commonly used dictionary should be interpreted as having a meaning consistent with the meaning in the context of the related art, and should not be interpreted in an ideal or excessively formal meaning unless explicitly defined in the present application. Hereinafter, example embodiments will be described in detail with reference to the accompanying drawings. Like reference numerals illustrated in the respective drawings designate like members.

FIG. 1 is a flowchart illustrating a method for processing a blood vessel image according to an example embodiment.

First, in step 110, a device for processing a blood vessel image may extract a target blood vessel from a blood vessel image. The target blood vessel may also be referred to as a main blood vessel. According to an example embodiment, an image receiver of the device for processing the blood vessel image may receive a blood vessel image photographed by a blood vessel image photographing device. The blood vessel image is an image obtained by photographing a blood vessel of a living body and may be generated using a coronary angiography (hereinafter, CAG) image and/or a magnetic resonance imaging (MRI). For example, the blood vessel image may be an image obtained by performing X-ray imaging of a living body into which a contrast agent is injected.

According to an example embodiment, the device for processing the blood vessel image may extract a target blood vessel from the blood vessel image on the basis of a machine learning model. The machine learning model is at least one model having a machine learning structure designed to extract the target blood vessel from the blood vessel image in response to an input of the blood vessel image, and for example, may include a neural network. The device for processing the blood vessel image may calculate an extraction result of the target blood vessel by performing an operation according to the above-described machine learning model on the received blood vessel image. For example, output data of the machine learning model may include a score corresponding to a possibility (e.g., probability) that each pixel in a plurality of pixels of the blood vessel image indicates the target blood vessel. The device for processing the blood vessel image may generate an extraction result of the target blood vessel by determining pixels having a score of a threshold value or more in output data as the target blood vessel. As another example, the output data of the machine learning model is a target blood vessel area segmented from the blood vessel image, and may include pixels extracted as the target blood vessel among the plurality of pixels of the blood vessel image. The extraction result of the target blood vessel may be, for example, a set of pixels extracted as the target blood vessel of pixels of the blood vessel image and/or an image (e.g., a target blood vessel image) corresponding to the target blood vessel area segmented from the blood vessel image.

For reference, the neural network may include a deep neural network (DNN). The DNN may include a fully connected network, a deep convolutional network, a recurrent neural network, and the like. The neural network may perform object classification, object recognition, radar image recognition, and the like by mapping input data and output data in a non-linear relationship to each other based on deep learning. The deep learning is a machine learning technique for solving problems such as object recognition from a big data set and may map input data and output data to each other through supervised or unsupervised learning. In the case of the supervised learning, the aforementioned machine learning model may be trained on the basis of training data including a pair of a training input (e.g., a blood vessel image for training) and a training output (e.g., a ground truth image segmented to the target blood vessel by experts and the like with respect to the blood vessel image for training) mapped in the corresponding training input. For example, the machine learning model may be trained to output the training output from the training input. The machine learning model (hereinafter, a 'temporary model') during training may generate a temporary output in response to the training input, and may be trained so that a loss between the temporary output and the training output (e.g., a ground truth value) is minimized. During the training process, parameters (e.g., connection weights between nodes/layers in the neural network) of the machine learning model may be updated according to the loss.

However, an example in which the machine learning model directly extracts the target blood vessel from the blood vessel image has been described, but the present disclosure is not limited thereto. For example, the machine learning model may include a whole blood vessel extraction model and a target blood vessel extraction model. The whole vessel extraction model may be a model designed to extract a whole blood vessel area from the blood vessel image. The target blood vessel extraction model may be a model designed to extract a target blood vessel area from an image (e.g., a whole blood vessel image) indicating the whole blood vessel area. In addition, instead of the whole vessel extraction model, the device for processing the blood vessel image may also extract the whole blood vessel area by detecting a boundary on the basis of a difference in grayscale level between pixels in the blood vessel image and neighboring pixels. Illustratively, the device for processing the blood vessel image may detect the corresponding pixel as a boundary when a gradient value of grayscale levels of an arbitrary pixel and neighboring pixels is greater than a threshold gradient value. Accordingly, the device for processing the blood vessel image may detect a region in which the grayscale level is rapidly changed as the boundary. The device for processing the blood vessel image may also extract a target blood vessel image using the target blood vessel extraction model from the whole blood vessel image extracted on the basis of the gradient value of the grayscale level.

Furthermore, the device for processing the blood vessel image may also selectively use a machine learning model to be used for extraction of the target blood vessel from among a plurality of machine learning models according to the shape and type of the blood vessel and/or a blood vessel area. According to an example embodiment, the device for processing the blood vessel image may store a plurality of machine learning models for each type of blood vessel (e.g., left main coronary artery (LM), left anterior descending artery (LAD), left circumflex artery (LCX), and right coronary artery (RCA)) and/or for each blood vessel area (e.g., proximal region, mid region, and distal region). For reference, the blood vessel area may be classified into a proximal portion, a middle portion, and a distal portion according to a distance from a blood vessel point into which a catheter is inserted, but is not limited thereto. The blood vessel area may also be classified according to a ratio of a distance from a point where the contrast agent is injected into a blood vessel insertion unit and a distance from a blood vessel end into which the contrast agent may be injected in order to obtain the blood vessel image. For example, the device for processing the blood vessel image may select a type of blood vessel to be extracted and load a machine learning model corresponding to the identified type of blood vessel. The device for processing the blood vessel image may generate an extraction result of a target blood vessel corresponding to the type of blood vessel selected from the blood vessel image using the loaded machine learning model. Illustratively, the device for processing the blood vessel image may store a machine learning model corresponding to a plurality of cardiovascular types (e.g., one right coronary artery and two left coronary arteries). Each of the machine learning models corresponding to the plurality of cardiovascular types may be trained on the basis of training data corresponding to the corresponding cardiovascular type. Trained parameters of the machine learning models for each cardiovascular type may be different from each other, and furthermore, machine learning structures (e.g., convolutional neural networks, U-net structures, etc.) may be different from each other. For convenience of description, the machine learning models in which parameters and/or machine learning structures are distinguished for each type of blood vessel have been described, but the present disclosure is not limited thereto. The device for processing the blood vessel image may also be used for extracting the target blood vessel by storing the plurality of machine learning models that are distinguished from each other by the shape and type of the blood vessel, and/or the blood vessel area and selectively loading a required blood vessel model.

In addition, in step 120, the device for processing the blood vessel image may determine a region of interest (ROI) for the extraction result of the target blood vessel on the basis of a first input received from the user. The ROI may indicate a partial region selected by the user in the blood vessel image for analysis of the blood vessel image. The device for processing the blood vessel image may focus processing on the blood vessel image on the ROI by determining the ROI. The detailed description of the ROI will be described below in FIG. 2.

In step 130, the device for processing the blood vessel image may identify an error portion of the extraction result on the basis of a second input received from the user within the determined ROI and correct the identified error portion. The error portion may include a discontinuity portion and/or a misidentification portion. The discontinuity portion may indicate a portion where among target blood vessel areas extracted as the target blood vessel and/or pixels indicating the target blood vessel, at least one area and/or at least one pixel is separated or spaced apart from other areas and/or other pixels. The misidentification portion may indicate a portion where an area and/or pixels corresponding to a blood vessel other than the target blood vessel to be actually extracted from the blood vessel image are erroneously extracted as the target blood vessel.

For example, the device for processing the blood vessel image may identify and correct an error portion on the basis of a movement trajectory of the second input in response to a case where a point at which the second input is detected moves within the ROI. As another example, the second input may represent a pointing input. The device for processing the blood vessel image may also identify and correct an error portion on the basis of a region between a start point and an end point corresponding to the pointing input. As another example, the device for processing the blood vessel image may identify and correct a point at which the second input is maintained as the error portion, in response to a case where the point at which the second input is detected is maintained for a threshold time or more at a point within the ROI. The correction on the basis of the second input will be described with reference to FIGS. 4 to 6 below.

Figure 2A:
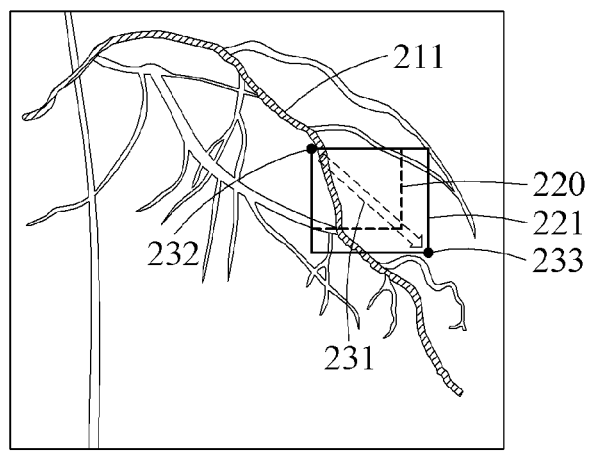
FIGS. 2A to 2C are diagrams illustrating blood vessel images in which a target blood vessel and a region of interest (ROI) are displayed, according to an example embodiment.
Figure 2B:
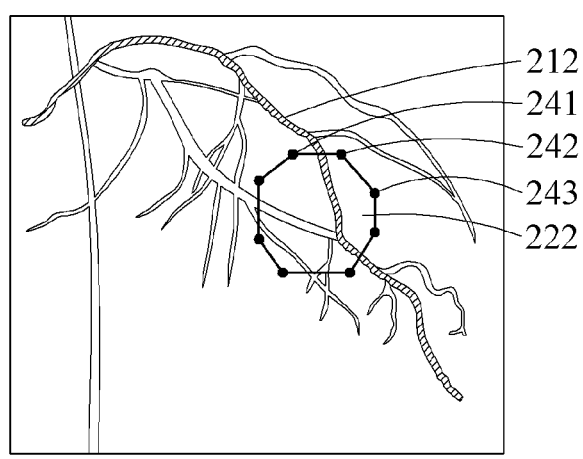
Figure 2C:
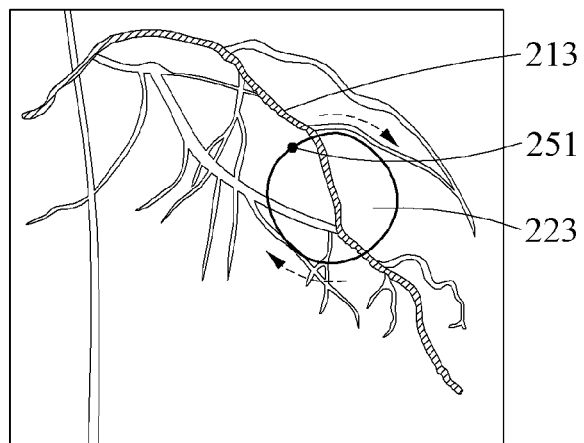

FIGS. 2A to 2C are diagrams illustrating blood vessel images in which a target blood vessel and a region of interest (ROI) are displayed, according to an example embodiment.

The device for processing the blood vessel image may photograph blood vessel images 201, 202, and 203. The device for processing the blood vessel image may receive the blood vessel images 201, 202, and 203 from a blood vessel image photographing device. The device for processing the blood vessel image may extract target blood vessels 211, 212, and 213 from the received blood vessel images 201, 202, and 203. The device for processing the blood vessel image may extract the target blood vessels 211, 212, and 213 on the basis of a machine learning model. The device for processing the blood vessel image may determine a region of interest (ROI) 221 for the extraction result of the target blood vessel on the basis of a first input 231 received from the user. The device for processing the blood vessel image may determine a shape of the ROI on the basis of points at which the first input is detected. The device for processing the blood vessel image may detect a start point 232 of the first input 231 and an end point 233 of the first input 231 received from the user. The first input 231 may be detected at the start point 232 and then maintained until the end point 233 and released at the end point 233.

Referring to FIG. 2A, the device for processing the blood vessel image may receive a drag input from the start point 231 to the end point 233 as the first input 231 from the user. The drag input may represent an input of clicking or touching any point (e.g., the start point 232) on the display, moving while the click or touch is maintained, and releasing the click or touch at another point (e.g., the end point 233). In addition, the device for processing the blood vessel image may determine the ROI 221 in a predefined shape between the detected start point 232 and end point 233. For example, the ROI 221 may be determined such that the start point 232 and the end point 233 are disposed on a boundary of the ROI 221. As illustrated in FIG. 2A, the predefined shape of the ROI 221 may be a rectangle, but is not limited thereto, and may be a polygon or a circle. The device for processing the blood vessel image may output a temporary ROI 220, which is a region between a point where the detection of the first input 231 starts and a point where the first input 231 is currently detected, through the display, to provide the output temporary ROI 220 to the user. The device for processing the blood vessel image may provide feedback to the user before determining the ROI 221 by providing the temporary ROI 220 to the user. When the detection of the first input 231 ends, the device for processing the blood vessel image may determine the ROI 221 in a predefined shape between the start point 232 where the first input 231 is detected and the end point 233 of the first input 231 to output and provide the determined ROI 221 to the user through the display.

Referring to FIG. 2B, the device for processing the blood vessel image may receive a first input including a plurality of inputs from the user. The plurality of inputs included in the first input may represent a click or a touch on an arbitrary point on the display. The device for processing the blood vessel image may determine, as the ROI 222, a region in a polygon formed by continuously connecting points 241, 242, and 243 on the display corresponding to the plurality of inputs in a straight line according to a user input, according to the first input received from the user. The device for processing the blood vessel image may provide the user with a partial shape of a polygon formed from the point where the detection of the first input starts to the point where the first input is currently detected.

Referring to FIG. 2C, the device for processing the blood vessel image may receive, as the first input, a drag input from a start point 251 to an end point 251 which is the same point as the start point from the user. The device for processing the blood vessel image may determine, as a ROI 223, a region in a free curve corresponding to a drag input of the user having the same start point and end point. The device for processing the blood vessel image may provide the user with a partial shape of a free figure formed by the free curve formed from the point where the detection of the first input starts to the point where the first input is currently detected.

When there are blood vessel branches extracted as the target blood vessel within the ROI determined on the basis of the first input received from the user, the device for processing the blood vessel image may fix an upper branch of the upper branch and a lower branch adjacent to each other based on one branch point included in the ROI as a correct region branch. The correct region branch may represent a blood vessel branch which is not identified as the error portion or not desired to be corrected by the user in the target blood vessel extracted by the device for processing the blood vessel image. The device for processing the blood vessel image may identify and correct the error portion only with respect to the lower branches based on the upper branch fixed as the correct region branch.

The device for processing the blood vessel image according to another example embodiment may also correct the ROI determined on the basis of the first input received from the user according to a predetermined condition. For example, the predetermined condition may indicate that the ROI intersects at least one correct region branch which does not correspond to the error portion or is not desired to be corrected by the user in the target blood vessel extracted by the device for processing the blood vessel image in a part of the boundary of the ROI. Illustratively, the device for processing the blood vessel image can perform a correction of extending or moving the ROI so as to intersect the at least one correct region branch which does not correspond to the error portion or is not desired to be corrected by the user in the target blood vessel extracted by the device for processing the blood vessel image in the part of the boundary of the ROI determined on the basis of the first input received from the user. The device for processing the blood vessel image may correct the ROI so that the correct region branch among the blood vessel branches in the ROI and the ROI intersect each other at an upper boundary of the ROI. However, the present disclosure is not limited thereto, and the ROI may be corrected to intersect the target blood vessel at any position on the boundary of the ROI. In addition, the device for processing the blood vessel image may also receive the first input from the user again when the extracted target blood vessel is not included in the ROI determined on the basis of the first input received from the user at all.

The device for processing the blood vessel image may identify and correct an error portion based on a branch point. The branch point may indicate a point at which two or more blood vessel branches are combined and/or a point at which the blood vessel is divided into a plurality of blood vessel branches. A blood vessel area captured in the blood vessel image 200 may have a plurality of branch points.

In order to finally determine the target blood vessel 210 as illustrated in FIG. 2, the device for processing the blood vessel image according to an example embodiment may perform the extraction of the target blood vessel 210, the determination of the ROI 220, and the identification and correction of the error portion of the extraction result within the determined ROI 220.

Figure 3:
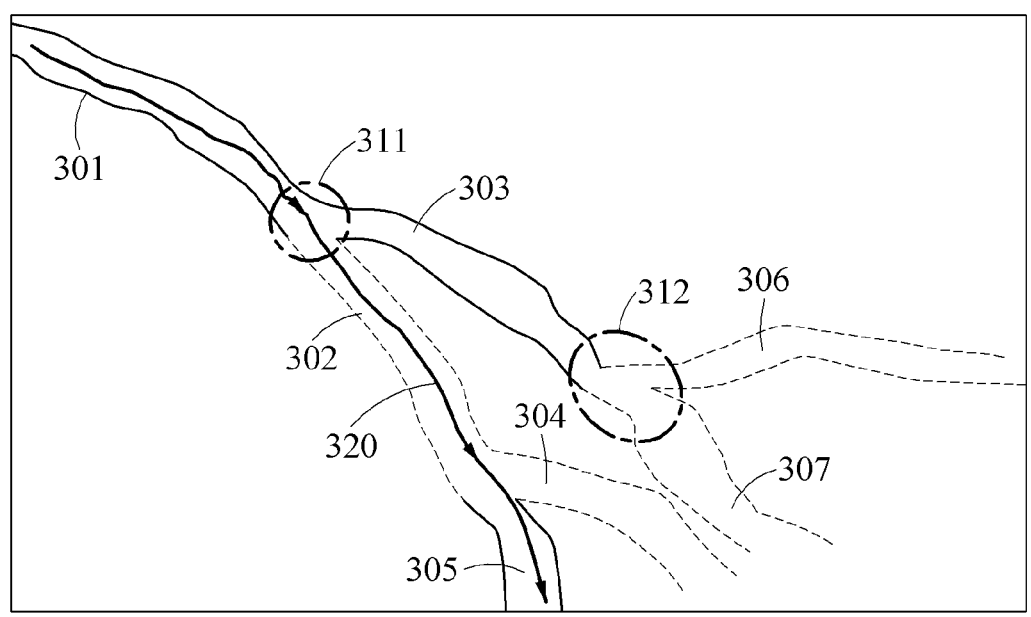
FIG. 3 illustrates an example in which an error portion occurs in an extraction result of a target blood vessel according to an example embodiment.

FIG. 3 illustrates an example in which an error region occurs in an extraction result of a target blood vessel according to an example embodiment.

The device for processing the blood vessel image according to an example embodiment may identify branch points and branches from the blood vessel image. For example, the device for processing the blood vessel image may extract a whole blood vessel area and identify the branch points and the branches from the extracted whole blood vessel area. The device for processing the blood vessel image may identify blood vessel branches based on the branch point. The whole blood vessel area may be extracted from the blood vessel image. The device for processing the blood vessel image according to an example embodiment may extract the whole blood vessel area from the blood vessel image on the basis of a whole vessel extraction model. As described above, the whole blood vessel extraction model may be a model trained to generate output data indicating a result in which the blood vessel area and the remaining non-blood vessel area are divided from the blood vessel image.

FIG. 3 illustrates a portion 300 corresponding to the ROI 220 of the blood vessel image 200 illustrated in FIG. 2 in the extracted whole blood vessel area. The device for processing the blood vessel image may identify blood vessel branches based on the branch points within the ROI 220. For reference, in the present specification, an upper blood vessel branch may indicate a branch before the branch point according to a progress direction of a blood flow or a progress direction of the contrast agent, and a lower blood vessel branch may indicate a branch after the branch point. For example, as a result identified by the device for processing the blood vessel image, first to seventh branches 301 to 307 and branch points 311 and 312 are illustrated. Based on the first branch point 311, the first branch 301 may be an upper blood vessel branch, and the second branch 302 and the third branch 303 may be lower blood vessel branches. In addition, a relationship between the upper blood vessel branch and the lower blood vessel branches is relative, and may vary for each branch point. For example, the second branch 302 may be an upper blood vessel branch with respect to the fourth branch 304 and the fifth branch 305. The device for processing the blood vessel image may generate blood vessel structure data by generating and indexing nodes corresponding to each of the blood vessel branches. The blood vessel structure image will be described below in FIG. 9 below.

In an example illustrated in FIG. 3, the device for processing the blood vessel image may extract the first branch 301, the third branch 303, and the fifth branch 305 as blood vessel branches belonging to the target blood vessel. However, a blood vessel path 320 corresponding to the target blood vessel 220 illustrated in FIG. 2 passes through the first branch 301, the second branch 302, and the fifth branch 305. Accordingly, in the extraction result of the exemplary target blood vessel, the first branch point 311 directed from the first branch 301 to the third branch 303 may be an error portion. The detection and correction of the error portion will be described below.

Figure 4:
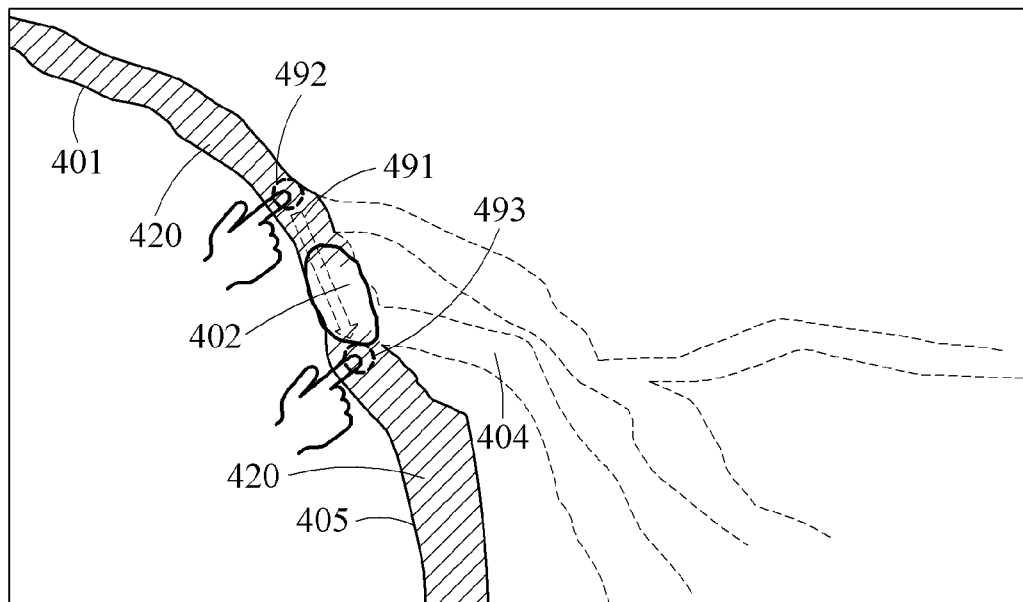
FIGS. 4 to 6 illustrate a method for identifying an error portion of the extraction result and correcting the identified error portion on the basis of a second input received from a user in an ROI.
Figure 5:
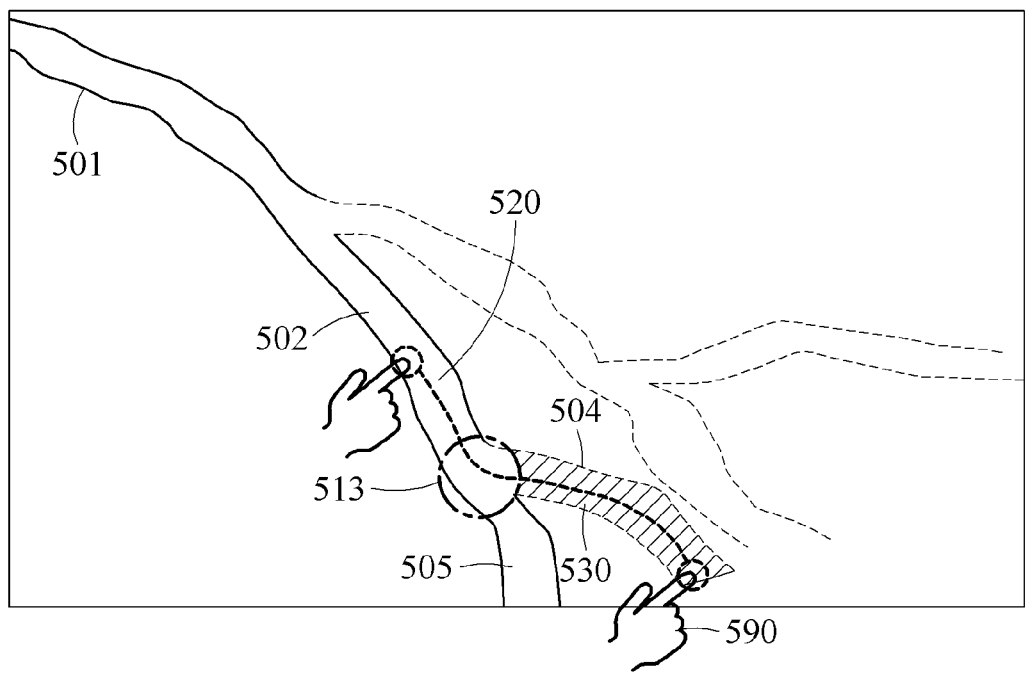
Figure 6:
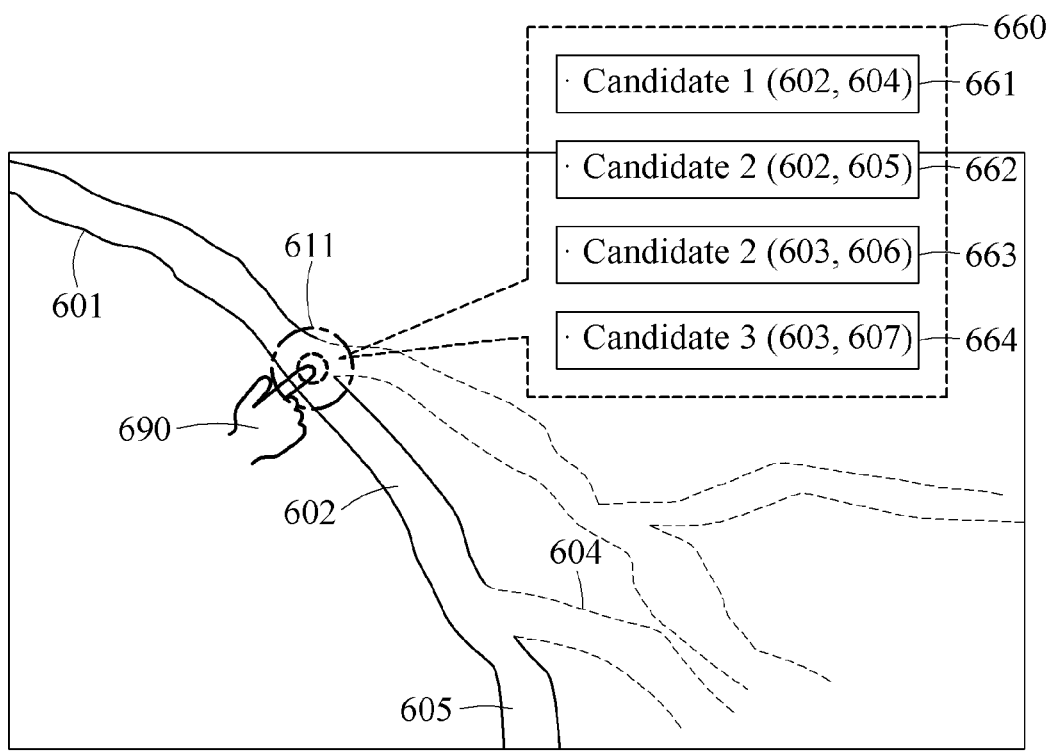

FIGS. 4 to 6 illustrate a method for identifying an error portion of the extraction result and correcting the identified error portion on the basis of the second input received from the user within the ROI.

FIG. 4 illustrates a method for identifying and correcting a discontinuity portion of the extraction result on the basis of the second input received from the user by the device for processing the blood vessel image according to an example embodiment. The device for processing the blood vessel image may correct an error portion on the basis of a plurality of points of the second input, in response to a case where the second input is detected from the plurality of points within the ROI.

The second input received from the user by the device for processing the blood vessel image according to an example embodiment may represent a drag input. The device for processing the blood vessel image may identify and correct an error portion on the basis of a movement trajectory of a second input 491 in response to the case in which a point at which the second input is detected moves within the ROI. While a point corresponding to the second input 491 moves along a region extracted as the target blood vessel, the device for processing the blood vessel image may detect whether there is a discontinuity portion at points through which the second input 491 passes. Illustratively, when the device for processing the blood vessel image first extracts blood vessel branches 401 and 405 as a target blood vessel and the point corresponding to the second input 491 of the user moves along the region 420 extracted as the target blood vessel, the device for processing the blood vessel image may detect whether there is a discontinuity portion at the points through which the second input 491 passes. For reference, the device for processing the blood vessel image may determine that the point corresponding to the second input 491 moves along the region extracted as the target blood vessel even if the point corresponding to the second input 491 deviates from the region extracted as the target blood vessel for a moment. For example, the device for processing the blood vessel image may determine that the second input 491 is maintained in the region 420 when the second input 491 moves to a point out of the aforementioned region 420 from the point other than the branch point within the region 420 extracted as the target blood vessel and returns to the region 420 again before a threshold time elapses. However, the device for processing the blood vessel image may determine that the second input 491 deviates from the region 420, in response to a case where the second input 491 moves to another branch out of the region 420 from the branch point within the region 420 extracted as the target blood vessel.

For example, the device for processing the blood vessel image may receive the second input 491 corresponding to the drag input between graphic points corresponding to two points included in the target blood vessel area extracted within the ROI from the user. The drag input may represent an input of clicking or touching a graphic point corresponding to one of two points included in the target blood vessel area by the user, moving in the clicked or touched state, and releasing the click or touch at a graphic point corresponding to the other point. The device for processing the blood vessel image may detect whether there is a discontinuity portion every points between the blood vessel branch corresponding to the start point of the second input 491 and the blood vessel branch corresponding to the end point of the second input 491, in response to the second input 491 received from the user. Accordingly, the device for processing the blood vessel image may continuously attempt to detect the discontinuity portion while the second input 491 moves along the region extracted as the target blood vessel. Illustratively, when the start point and the end point corresponding to the second input 491 received from the user are included in the regions corresponding to the blood vessel branches 401 and 405 and the point corresponding to the second input 491 moves along the region 420 extracted as the target blood vessel, the device for processing the blood vessel image may detect whether there is the discontinuity portion between the blood vessel branches 401 and 405. When the regions corresponding to the blood vessel branches 401 and 405 of the target blood vessel from which the blood vessel branches 401 and 405 are extracted are separated or spaced apart from each other, the device for processing the blood vessel image may determine the regions as the discontinuity portion. For example, the device for processing the blood vessel image may determine whether the corresponding points are included in the region 420 extracted as the target blood vessel while the second input 491 passes through the points between the blood vessel branches 401 and 405. In response to a case where the corresponding points are not included the region 420, the device for processing the blood vessel image may determine the corresponding points as the discontinuity portion. According to an example embodiment, the device for processing the blood vessel image may connect discontinued portions along the movement trajectory of the second input 491 in response to a case where the discontinuity portion is identified. For example, the device for processing the blood vessel image may connect the discontinued portions to each other with respect to the periphery and/or boundary of the blood vessel branches determined as the discontinuity portion. Illustratively, when the point corresponding to the second input 491 of the user moves along the region 420 extracted as the target blood vessel, the device for processing the blood vessel image may connect the regions corresponding to the blood vessel branches 401 and 405 determined as the discontinuity portion along the movement trajectory of the second input 491 received from the user. When the points corresponding to the second input 491 move along the region 402 between the discontinued blood vessel branches 401 and 405, the device for processing the blood vessel image may extract the region 402 between the discontinued blood vessel branches 401 and 405 as the target blood vessel. That is, the device for processing the blood vessel image may add the region 402 to the extraction result of the target blood vessel.

The second input received from the user by the device for processing the blood vessel image according to an example embodiment may represent a pointing input. The pointing input is an input indicating one point on the display and may include, for example, a click input by mouse operation and/or an input by touch operation to a touch display (e.g., touch input). However, the pointing input is not limited thereto, and may include a position indication input by various pointing devices (e.g., a trackball mouse, a touchpad, a trackpad, etc.) according to a design. The device for processing the blood vessel image may receive a pointing input for a start point and an end point as the second input from the user. However, the present disclosure is not limited thereto, and the device for processing the blood vessel image may also receive a pointing input of clicking or touching two or more points from the user. The device for processing the blood vessel image may identify and correct an error portion on the basis of a region between the start point and the end point of the pointing input according to the pointing input. Illustratively, the device for processing the blood vessel image may first extract the blood vessel branches 401 and 405 as the target blood vessel and detect whether there is a discontinuity portion in a blood vessel area between points 492 and 493 corresponding to the second input of the user.

For example, the device for processing the blood vessel image may receive the second input corresponding to the pointing input including the click or touch input for the two points 492 and 493 included in the target blood vessel area extracted within the ROI from the user. The device for processing the blood vessel image may detect whether there is the discontinuity portion every points between the blood vessel branch corresponding to the start point 492 of the second input and the blood vessel branch corresponding to the end point of the second input in response to the second input received from the user and correct the discontinuity portion in the same manner as the case of receiving the drag input as the second input.

FIG. 5 illustrates a method for identifying and correcting a misidentification portion of the extraction result on the basis of the movement trajectory of the input received from the user by the device for processing the blood vessel image according to an example embodiment. The device for processing the blood vessel image may determine a blood vessel branch located out of the region corresponding to the movement trajectory of the second input among the blood vessel branches extracted as the target blood vessel connected with the branch point as the misidentification portion, in response to a case where the point corresponding to a second input 590 moves from the branch point within the area extracted as the target blood vessel to an area out of the target blood vessel. When the device for processing the blood vessel image determines the portion related to the branch point as the misidentification portion, the ROI on the basis of the first input may be extended so that all the lower branches based on the branch point are included within the ROI. Illustratively, the device for processing the blood vessel image may first extract blood vessel branches 501, 502, and 505 as the target blood vessel and determine a portion related to a branch point 513 as the misidentification portion, when the point corresponding to the second input 590 of the user moves to a region 530 out of the target blood vessel from the branch point 513 within the region 520 extracted as the target blood vessel. For example, when the second input 590 moves to the region corresponding to the lower blood vessel branch 504 different from the lower blood vessel branch 505 first extracted as the target blood vessel based on the branch point 513, the device for processing the blood vessel image may determine that the point corresponding to the second input 590 received from the user moves to the region out of the target blood vessel. The device for processing the blood vessel image may determine at least one branch 505 of the blood vessel branches extracted as the target blood vessel adjacent to the branch point 513 as the misidentification portion in the extraction result for the target blood vessel.

The device for processing the blood vessel image may replace at least one of the blood vessel branches identified as the misidentification portion with a blood vessel branch indicated by the second input 590 out of the target blood vessel and correct the remaining extraction results on the basis of the replaced blood vessel branch. For example, when the points corresponding to the second input 590 move out of the region corresponding to the extracted target blood vessel, the device for processing the blood vessel image may replace the lower blood vessel branch 505 first extracted as the target blood vessel based on the branch point 513 with the blood vessel branch 504. The device for processing the blood vessel image may correct the extraction result of the target blood vessel on the basis of the replaced blood vessel branch 504. For example, the device for processing the blood vessel image may exclude blood vessel branches subsequent to the lower blood vessel branch 505 first extracted from the extraction result of the target blood vessel and add the blood vessel branches subsequent to the replaced blood vessel branch 504 to the extraction result of the target blood vessel.

FIG. 6 illustrates a method for providing correction candidates to the user on the basis of a second input 690 received from the user and identifying and correcting an error portion according to a selection input of the user. When the second input 690 is detected for a first threshold time or more at the point in the region corresponding to the extraction result of the target blood vessel, the device for processing the blood vessel image may determine the corresponding point as the error portion. The device for processing the blood vessel image may provide correction candidates corresponding to the point determined as the error portion to the user. The correction candidates may represent a set of candidate blood vessel branches having a shape capable of replenishing the discontinuity portion or a set of candidate blood vessel branches having a shape and a structure capable of replacing the misidentification portion, when the point where the second input 690 is maintained is determined as the error portion. For example, the device for processing the blood vessel image may determine the correction candidates on the basis of blood vessel structure data, curvature information of the blood vessel, diameter information of the blood vessel, brightness information of the blood vessel, and the like according to those illustrated in FIGS. 7 to 14 below. For example, a first correction candidate 661 may be a candidate branch determined on the basis of the blood vessel structure data, a second correction candidate 662 may be a candidate branch determined on the basis of the curvature information, a third correction candidate 663 may be a candidate branch determined on the basis of the diameter information, and a fourth correction candidate 664 may be a candidate branch determined on the basis of the brightness information. However, this is only illustrative, and the determination of the candidate branches may vary depending on a design. In addition, although the example of determining the point where the second input 690 is maintained as the error portion has been described above, the device for processing the blood vessel image may also determine the error portion on the basis of the blood vessel structure data, the curvature information of the blood vessel, the diameter information of the blood vessel, the brightness information of the blood vessel, and the like according to those illustrated below in FIGS. 7 to 14 with respect to the point where the second input 690 is maintained.

The device for processing the blood vessel image may select one of the correction candidates on the basis of a third input for selecting the correction candidates received from the user. The device for processing the blood vessel image may add blood vessel branches included in the selected correction candidates to the extraction result of the target blood vessel.

Illustratively, the device for processing the blood vessel image may first extract blood vessel branches 601, 602, and 605 as the target blood vessel. When the point where the second input 690 received from the user is detected is included in the region corresponding to a branch point 611, the device for processing the blood vessel image may output a graphic object 660 capable of providing the user with the selection for one of the correction candidates 661, 662, 663, and 664 corresponding to the branch point 611. The device for processing the blood vessel image may receive the third input selecting one of the correction candidates 661, 662, 663, and 664 from the user to extract the blood vessel branches (e.g., the blood vessel branches 602 and 604) consisting of the selected correction candidate as the target blood vessel.

When the point corresponding to the second input 690 is a point corresponding to a boundary (e.g., a blood vessel edge) of the extracted target blood vessel and the time when the second input 690 is detected at the corresponding point is a second threshold or more, the device for processing the blood vessel image may provide the user with correction candidates corresponding to the boundary. For example, the device for processing the blood vessel image may provide the user with an option of a correction candidate of smoothing softly the boundary, a correction candidate of emphasizing a contrast with a background, or a correction candidate of selecting a boundary different from the existing boundary, with respect to the boundary of the target blood vessel corresponding to the second input 690 received from the user.

The device for processing the blood vessel image may identify an error portion from the extraction result of the target blood vessel and correct the identified error portion in response to the determination of the ROI. The device for processing the blood vessel image may provide the user with the correction result of the error portion. The device for processing the blood vessel image may provide the user with the correction result of the error portion to correct the error portion by receiving the input corresponding to the correction result from the user and identify and correct the error portion on the basis of the second input 690 received from the user within the ROI in which the error portion is corrected. In other words, the device for processing the blood vessel image may perform a preprocessing process of providing the correction result to the user by identifying and correcting the error portion automatically by the processor, before the error portion is identified and corrected by receiving the second input 690 from the user within the ROI.

For reference, in FIGS. 4 to 6, the second inputs 491, 590, and 690 are illustrated as the touch input for convenience of description, but are not limited thereto, and may also include other types of inputs for pointing the points on the display, such as a click input.

Figure 7:
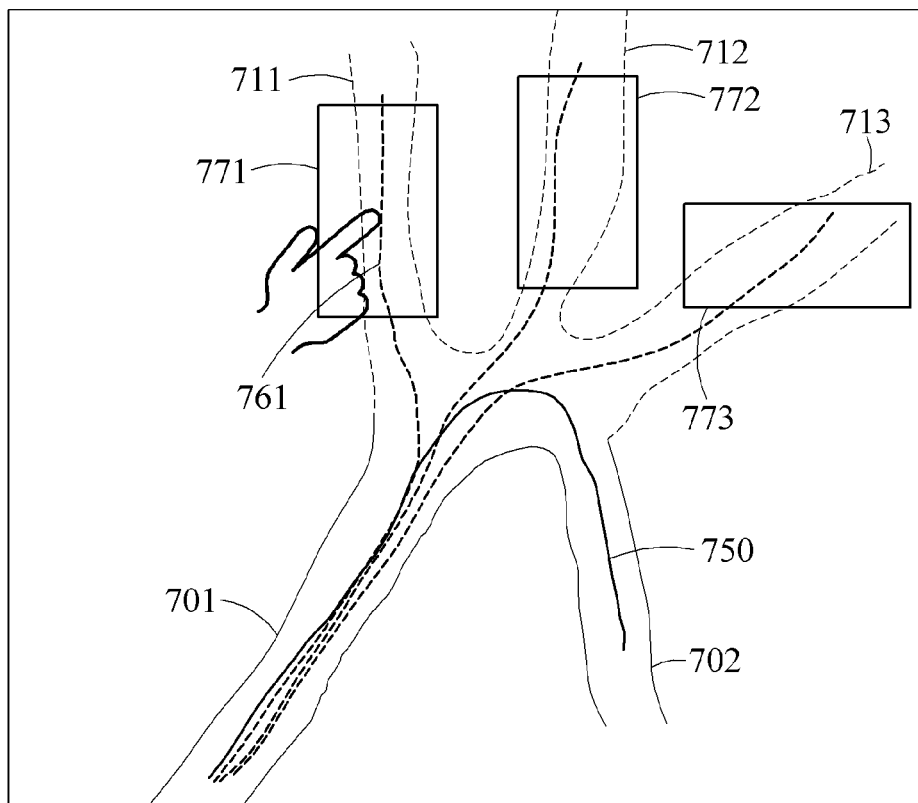
FIGS. 7 and 8 illustrate a method for correcting an error portion according to an example embodiment.
Figure 8:
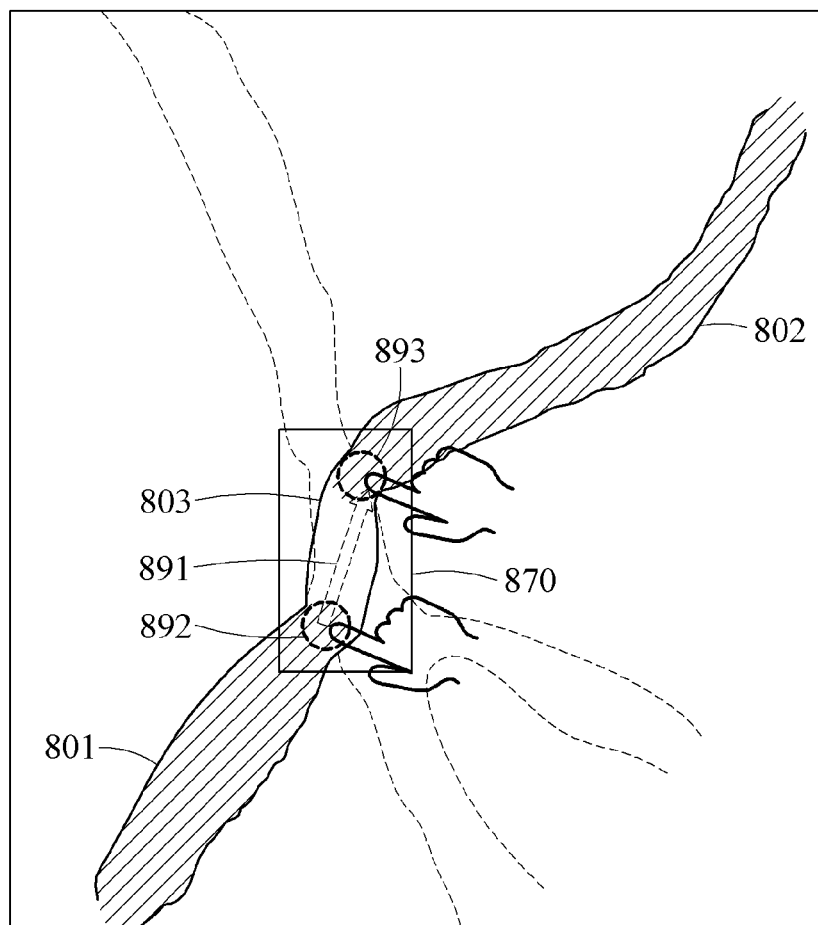

FIGS. 7 and 8 illustrate a method for correcting an error portion according to an example embodiment.

FIG. 7 illustrates a method for providing the user with a correction result of a misidentification portion when an error portion is identified from the extraction result of the target blood vessel and the identified error portion is the misidentification portion. According to an example embodiment, the device for processing the blood vessel image may correct the identified error portion on the basis of a user input (e.g., a touch input) when the error portion is identified in the target blood vessel. The device for processing the blood vessel image may provide one or more candidate branches to the user in response to a case where the error portion is the misidentification portion. In response to a case of receiving a pointing input for one branch among one or more candidate branches from the user, the device for processing the blood vessel image may replace a branch corresponding to the error portion with the selected branch. Illustratively, when the device for processing the blood vessel image first extracts blood vessel branches 701 and 702 as a target blood vessel, the device for processing the blood vessel image may determine at least one branch of the blood vessel branches 701 and 702 as an error portion in the extraction result for the target blood vessel on the basis of at least one of blood vessel structure data related to the target blood vessel, curvature information of the target blood vessel, diameter information of the target blood vessel, and brightness information of the target blood vessel. The device for processing the blood vessel image may provide the user with one or more candidate blood vessel branches 711, 712, and 713 which are not extracted as the target blood vessel, when the identified error portion is the misidentification portion. An input/output interface of the device for processing the blood vessel image may output graphic objects 771, 772, and 773 that can provide the user with a selection of the candidate blood vessel branches 711, 712, and 713 through a display. The graphic objects may have a shape surrounding regions corresponding to the candidate blood vessel branches. In FIG. 7, the graphic objects 771, 772, and 773 are illustrated in a rectangular shape, but the shape is not limited thereto. The user may select a candidate blood vessel branch through a pointing input of simply clicking or touching a point corresponding to one of the graphic objects corresponding to the candidate blood vessel branches output on the display. That is, when the device for processing the blood vessel image detects a user input with respect to a point corresponding to the graphic object, the device for processing the blood vessel image may determine that a candidate blood vessel branch corresponding to the graphic object is selected, and may replace the blood vessel branch corresponding to the error portion with a selected candidate blood vessel branch. Illustratively, when the device for processing the blood vessel image detects the user input for a point corresponding to the graphic object 771 from the user, the device for processing the blood vessel image may extract the candidate blood vessel branch 711 corresponding to the graphic object 771 as the target blood vessel. That is, the device for processing the blood vessel image may replace the blood vessel branch 702 with the blood vessel branch 711 in the extraction result of the target blood vessel.

FIG. 8 illustrates a method for providing the user with a correction result of a discontinuity portion when an error portion is identified from the extraction result of the target blood vessel and the identified error portion is the discontinuity portion. The device for processing the blood vessel image according to an example embodiment may provide a blood vessel area including the discontinuity portion to the user in response to a case where the error portion identified in the target blood vessel is the discontinuity portion. The device for processing the blood vessel image may connect a region corresponding to a blood vessel branch corresponding to a start point of the user input and a region corresponding to a blood vessel branch corresponding to an end point of the user input, in response to a case where the user input is detected in a plurality of points with respect to a correction result.

In response to a drag input 891 received from the user with respect to the correction result, the device for processing the blood vessel image according to an example embodiment may connect a region corresponding to a blood vessel branch corresponding to a start point of the drag input 891 and a region corresponding to a blood vessel branch corresponding to an end point of the drag input 891. Illustratively, when the device for processing the blood vessel image first extracts blood vessel branches 801 and 802 as a target blood vessel, the device for processing the blood vessel image may determine regions corresponding to the blood vessel branches 801 and 802 of the extracted target blood vessel as discontinuity portions separated from each other. The input/output interface of the device for processing the blood vessel image may output a graphic object 870 related to the connection between the regions corresponding to the blood vessel branches 801 and 802 through a display. The graphic object 870 has a shape enclosing the region corresponding to at least a portion of the blood vessel branches 801 and 802 corresponding to the discontinuity portions and may represent that the blood vessel branches 801 and 802 are connectable by the user. The device for processing the blood vessel image may connect the regions corresponding to the blood vessel branches 801 and 802 selected by the drag input 891 and extract a blood vessel branch 803 between the discontinued blood vessel branches 801 and 802 as the target blood vessel, in response to the drag input 891 received from the user. The branches selected by the drag input 891 may indicate a blood vessel branch corresponding to a drag start point and a blood vessel branch corresponding to a drag end point. That is, the device for processing the blood vessel image may include the blood vessel branch 803 in the extraction result of the target blood vessel.

The device for processing the blood vessel image according to another example embodiment may connect regions corresponding to blood vessel branches corresponding to a start point 892 and an end point 893 of a pointing input, in response to the pointing input corresponding to two or more points received from the user with respect to the correction result. That is, the device for processing the blood vessel image may receive a click or touch input for the start point and the end point from the user. In response to the pointing input received from the user, the device for processing the blood vessel image may connect a region corresponding to the blood vessel branch 801 corresponding to the start point 892 of the pointing input and a region corresponding to the blood vessel branch 802 corresponding to the end point 893 of the pointing input.

Figure 9:
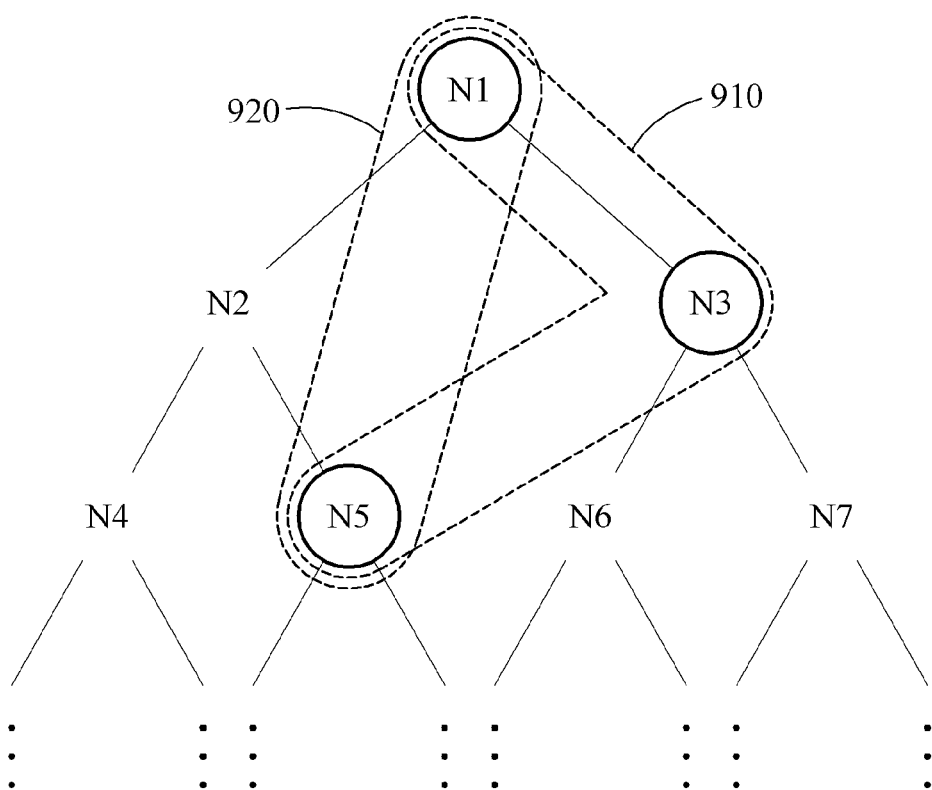
FIG. 9 illustrates a method for identifying an error in a target blood vessel using a topology of blood vessel structure data on the basis of nodes corresponding to blood vessel branches.

FIG. 9 illustrates a method of identifying an error in a target blood vessel using a topology of blood vessel structure data based on nodes corresponding to blood vessel branches.

According to an example embodiment, the device for processing the blood vessel image may identify an error portion on the basis of blood vessel structure data 900 related to the target blood vessel. The blood vessel structure data 900 is topological data indicating the structure of a blood vessel, and may be, for example, tree structure data in which nodes corresponding to blood vessel branches are indexed. For example, the device for processing the blood vessel image may identify blood vessel branches based on blood vessel branch points with respect to the whole blood vessel area, generate nodes corresponding to each of the identified blood vessel branches, and generate the blood vessel structure data 900 on the basis of the indexing of the generated nodes.

When the upper blood vessel branch is branched to a plurality of lower blood vessel branches based on the branch point, the device for processing the blood vessel image may connect a node corresponding to the upper blood vessel branch and nodes corresponding to the lower blood vessel branches. The device for processing the blood vessel image may generate the blood vessel structure data 900 for the whole blood vessels by repeating the connection of the nodes to the branch points and the vessel blood branches identified from the blood vessel image. For example, in the blood vessel structure data 900 illustrated in FIG. 9, first to seventh nodes N1 to N7 may sequentially correspond to the first to seventh branches 301 to 307 illustrated in FIG. 3, respectively. The first node N1 may be an uppermost node, and the second node N2 and the third node N3 may be lower nodes of the first node N1. The remaining nodes may have similar top-down relationships.

The device for processing the blood vessel image according to an example embodiment may calculate node connection data 910 between the nodes corresponding to the blood vessel branches extracted as the target blood vessel from the blood vessel image. For example, the device for processing the blood vessel image may calculate the node connection data 910 connected with the first node N1, the third node N3, and the fifth node N5 from the extraction result of the target blood vessel illustrated in FIG. 3.

The device for processing the blood vessel image may identify an error portion of the target blood vessel by comparing the node connection data 910 with the blood vessel structure data 900. The device for processing the blood vessel image may detect a connection error between the nodes of the target blood vessel on the basis of the generated blood vessel structure data 900. The device for processing the blood vessel image may determine, as an error portion, blood vessel branches and/or branch points corresponding to the nodes in which the connection error is detected. The device for processing the blood vessel image may determine an error portion on the basis of nodes which are not matched with the blood vessel structure data 900 in the node connection data 910. Illustratively, the node connection data 910 extracted in FIG. 9 may indicate that the first node N1, the third node N3, and the fifth node N5 are sequentially connected. In the blood vessel structure data 900, the third node N3 is not connected to the fifth node N5. In other words, the device for processing the blood vessel image may determine that the connection between the third node N3 and the fifth node N5 in the node connection data 910 does not match the blood vessel structure data 900. The connection between the third node N3 and the fifth node N5 may be a connection error. The device for processing the blood vessel image may determine a blood vessel branch corresponding to at least one node of the nodes corresponding to the connection error as the error portion. For example, in FIG. 9, the device for processing the blood vessel image may determine a blood vessel branch corresponding to at least one of the third node N3 and the fifth node N5 as the error portion. In the above-described example, since the blood vessel branch corresponding to the third node N3 or the fifth node N5 is erroneously extracted as the target blood vessel, the blood vessel branch may be a misidentification portion.

As another example, the device for processing the blood vessel image may detect the blood vessel branch corresponding to a node missing from the node connection data 920 as a discontinuity portion on the basis of the blood vessel structure data 900. The device for processing the blood vessel image may calculate the node connection data 920 directly connected from the first node N1 to the fifth node N5. The device for processing the blood vessel image may detect that the second node N2 is missing from the node connection data 920 on the basis of the blood vessel structure data 900. In this case, the device for processing the blood vessel image may detect a blood vessel branch corresponding to the second node N2 as the discontinuity portion.

Figure 10:
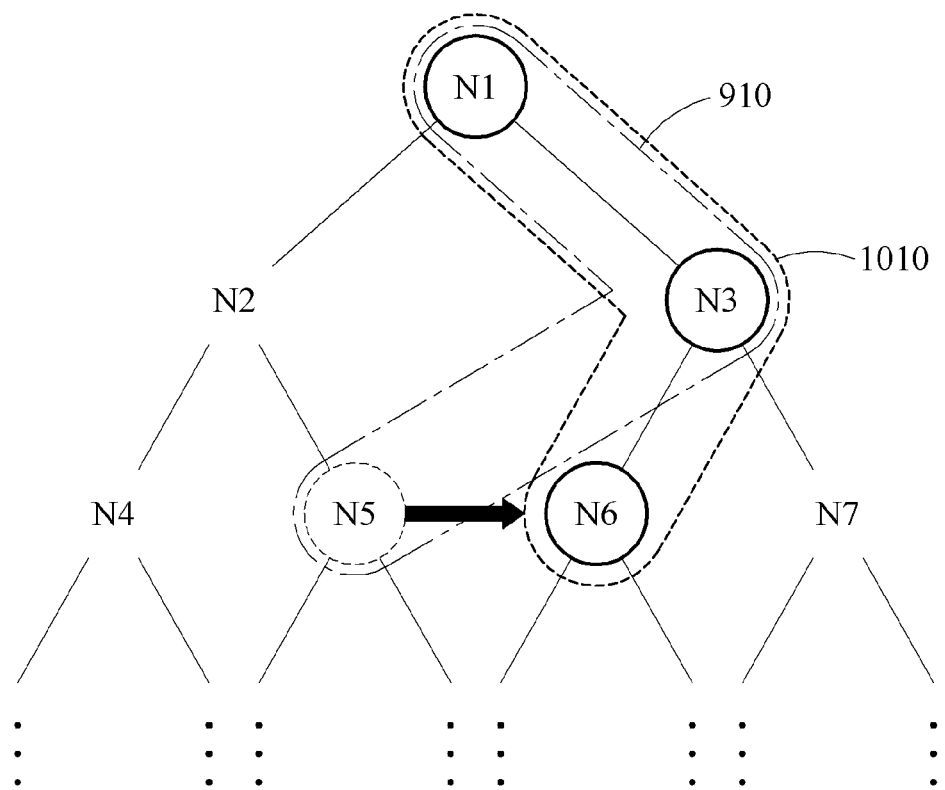
FIGS. 10 and 11 illustrate a method for correcting an error portion according to an example embodiment.
Figure 11:
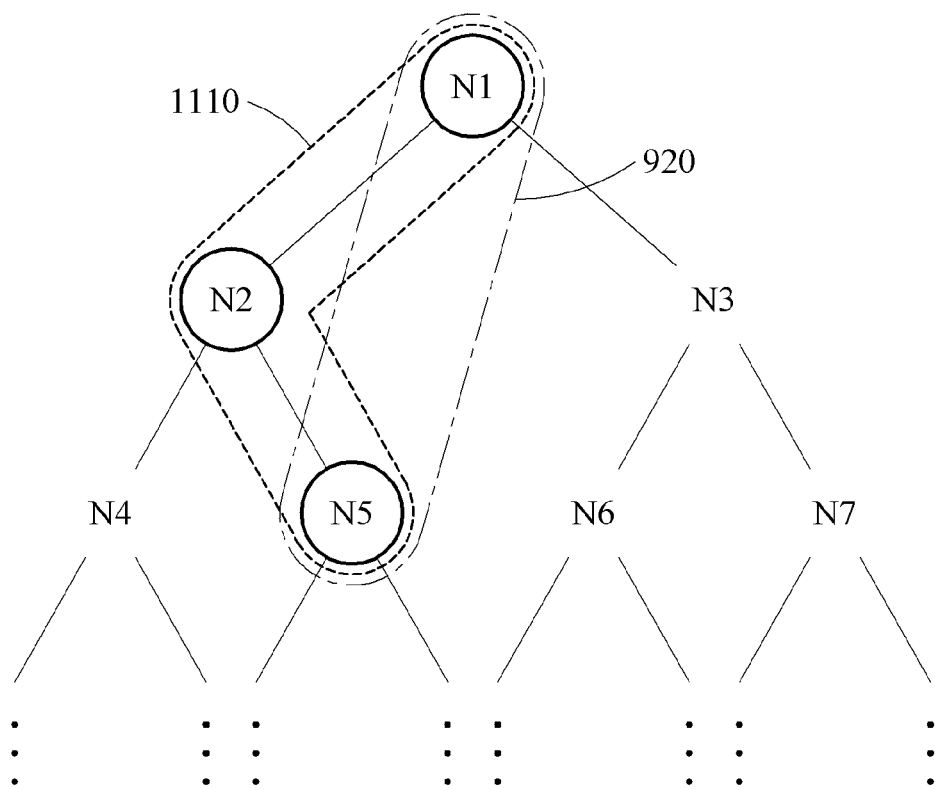

FIGS. 10 and 11 illustrate a method for correcting an error portion according to an example embodiment.

FIG. 10 illustrates a correction in the case where the node connection data 910 is calculated in FIG. 9. According to an example embodiment, in response to a case where the misidentification portion is identified, the device for processing the blood vessel image may replace a node corresponding to the misidentification portion with a node matching the blood vessel structure data. Illustratively, the device for processing the blood vessel image may determine that the fifth node N5 does not match the blood vessel structure data in the node connection data 910. The device for processing the blood vessel image may exclude the fifth node N5 that does not match the blood vessel structure data from the node connection data and add the sixth node N6 matching the blood vessel structure data to the node connection data to generate corrected node connection data 1010. Accordingly, the device for processing the blood vessel image may extract a blood vessel branch (e.g., a sixth branch 306 in FIG. 6) corresponding to the replaced sixth node N6 as the target blood vessel.

FIG. 11 illustrates a correction in the case where the node connection data 920 is calculated in FIG. 9. According to an example embodiment, the device for processing the blood vessel image may insert a connectable node between the nodes corresponding to the discontinuity portion in response to a case where the discontinuity portion is identified. Illustratively, the device for processing the blood vessel image may determine that a space between the first node N1 and the fifth node N5 is missing from the node connection data 920. The device for processing the blood vessel image may generate corrected node connection data 1110 by inserting the second node N2 between the nodes N1 and N5. The device for processing the blood vessel image may extract a blood vessel branch (e.g., the second branch 302 in FIG. 3) corresponding to the second node N2 as the target blood vessel.

As described above, by correcting the misidentification portion by replacing the nodes and adding the nodes, the device for processing the blood vessel image may remove a node connectivity error on the basis of a topology of the blood vessel structure data.

Figure 12:
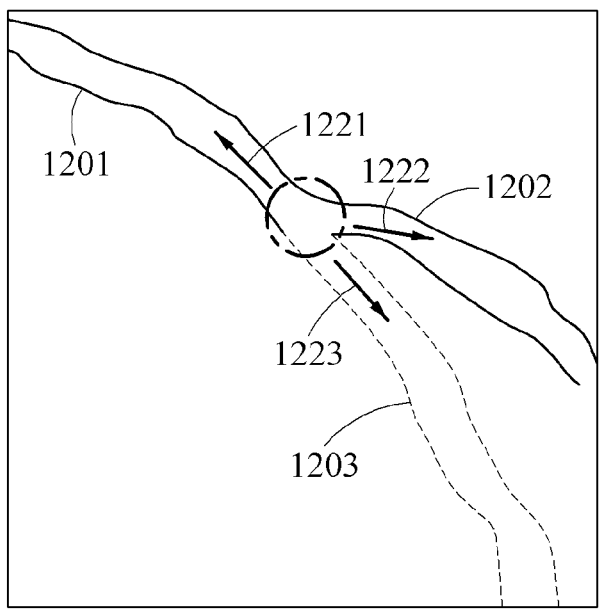
FIG. 12 illustrates a method for identifying and correcting an error in a target blood vessel using curvature information of the target blood vessel.

FIG. 12 illustrates a method for identifying and correcting an error in a target blood vessel using curvature information of the target blood vessel.

According to an example embodiment, the device for processing the blood vessel image may identify and correct a misidentification portion by using a curvature between blood vessel branches adjacent to each other in the target blood vessel. For example, the device for processing the blood vessel image may determine branches adjacent to each other as a misidentification portion in response to a case where a curvature between the branches adjacent to each other in the target blood vessel exceeds a threshold curvature. Illustratively, when the device for processing the blood vessel image first extracts blood vessel branches 1201 and 1202 as a target blood vessel, the device for processing the blood vessel image may calculate a curvature between the blood vessel branches 1201 and 1202. The device for processing the blood vessel image may determine at least one branch of the above-described blood vessel branches 1201 and 1202 as the misidentification portion in the extraction result for the target blood vessel in response to a case where the calculated curvature exceeds the threshold curvature. The blood vessel branches adjacent to each other in the target blood vessel to be actually extracted from the blood vessel image have a relatively small curvature. Accordingly, there is a possibility that the blood vessel branches adjacent to each other having a curvature exceeding the threshold curvature may be the error portion.

The device for processing the blood vessel image may correct the identified error portion, in response to a case where the error portion is identified in the target blood vessel using the threshold curvature. The device for processing the blood vessel image may replace one branch of the branches adjacent to each other with a candidate branch having a curvature with the remaining branches of the threshold curvature or less, with respect to the identified error portion. The candidate branch may represent one or more remaining branches that are not extracted as the target blood vessel among a plurality of blood vessel branches connected to one blood vessel branch based on an arbitrary branch point. Illustratively, when the curvature between the upper blood vessel branch 1201 and the blood vessel branch 1203 which is not extracted as the target blood vessel is the threshold curvature or less, the device for processing the blood vessel image may extract the blood vessel branch 1203 instead of the blood vessel branch 1202 as the target blood vessel. The device for processing the blood vessel image may replace the blood vessel branch 1202 with the blood vessel branch 1203 in the extraction result of the target blood vessel. Furthermore, when correcting the identified error portion, the device for processing the blood vessel image may apply a different threshold curvature according to a type of blood vessel (e.g., left main coronary artery (LM), left anterior descending artery (LAD), left circumflex artery (LCX), and right coronary artery (RCA)) or a blood vessel area (e.g., proximal region, mid region, and distal region).

The device for processing the blood vessel image may perform principal direction component analysis (e.g., principal component analysis (PCA)) of a blood vessel branch in order to analyze a difference in curvature. The device for processing the blood vessel image may analyze a principal direction component for each of the blood vessel branches divided based on the branch point. The principal direction component of the blood vessel branch may represent a component representing a direction of the corresponding blood vessel branch. For example, the device for processing the blood vessel image may obtain a principal direction vector for each of the blood vessel branches by using the principal direction component analysis for each of the blood vessel branches. The principal direction vector is a vector having a direction component representing a direction in which the blood vessel branch extends from the branch point, and may have a size of a unit vector. For example, the principal direction vector for any blood vessel branch may indicate a direction of the principal components of vector components directed from the branch point to points corresponding to the blood vessel branch. For example, the principal direction vectors of the blood vessel branches 1201, 1202, and 1203 may correspond to vectors 1221, 1222, and 1223, respectively. The device for processing the blood vessel image may determine branches adjacent to each other as a misidentification portion, in response to a case where inner product values of the principal direction vectors of the blood vessel branches adjacent to each other in the target blood vessel exceed a threshold value.

Illustratively, when inner product values of the principal direction vectors 1221 and 1222 of the blood vessel branches 1201 and 1202 adjacent to each other exceed the threshold value in the target blood vessel, the device for processing the blood vessel image may determine the blood vessel branches 1201 and 1202 adjacent to each other as the misidentification portion. Since the principal direction vector of each of the blood vessel branches has the size of a unit vector, the inner product values of the principal direction vectors may depend on angles between the vectors. As a result, since the principal direction vector corresponding to the upper branch and the principal direction vector corresponding to the lower branch are directed in opposite directions, the inner product of the two principal direction vectors has a negative value. Accordingly, when the inner product values of the principal direction vectors are a threshold value or more, it may be meant that the curvature between the blood vessel branches is large. The target blood vessel to be actually extracted from the blood vessel image is one blood vessel and has generally no large curvature change between the blood vessel branches adjacent to each other. Accordingly, when the inner product value of the principal direction vector between the blood vessel branches adjacent to each other exceeds the threshold value, the device for processing the blood vessel image may extract blood vessels other than the target blood vessel to be actually found. Furthermore, in the correcting of the identified error portion, the device for processing the blood vessel image may apply different threshold values according to a type of blood vessel or a blood vessel area.

The device for processing the blood vessel image may obtain a principal direction vector for each blood vessel branch segmented based on the branch point with respect to the extracted target blood vessel, but may also obtain a principal direction vector for each piece segmented in a predetermined length by segmenting the blood vessel in the predetermined length. The device for processing the blood vessel image may also identify an error portion in the target blood vessel by comparing principal directions of adjacent pieces with respect to the extracted target blood vessel to find a portion in which the curvature is greater than or equal to a threshold value. In other words, the device for processing the blood vessel image may segment the extracted target blood vessel in a threshold length or less. The device for processing the blood vessel image may determine pieces adjacent to each other as the misidentification portion, in response to a case where inner product values of the principal direction vectors of the pieces adjacent to each other segmented in the predetermined length exceed the threshold value. Since the device for processing the blood vessel image may calculate a curvature between the adjacent pieces by segmenting the target blood vessel in a threshold length or less, the device for processing the blood vessel image may identify the error portion of the target blood vessel more accurately than a case of identifying the error portion of the target blood vessel according to the blood vessel branches segmented based on the branch point.

The device for processing the blood vessel image may correct the identified error portion in response to a case where the error portion is identified in the target blood vessel using the principal direction vector. The device for processing the blood vessel image may replace one branch of the branches adjacent to each other with a candidate branch having an inner product value of the principal direction vector with the remaining branches of the threshold value or less, with respect to the identified error portion. Illustratively, when the inner product value of principal direction vectors 1223 and 1221 between the upper blood vessel branch 1201 and the blood vessel branch 1203 which is not extracted as the target blood vessel is the threshold value or less, the device for processing the blood vessel image may extract the blood vessel branch 1203 instead of the blood vessel branch 1202 as the target blood vessel. The device for processing the blood vessel image may replace the blood vessel branch 1202 with the blood vessel branch 1203 in the extraction result of the target blood vessel.

Figure 13:
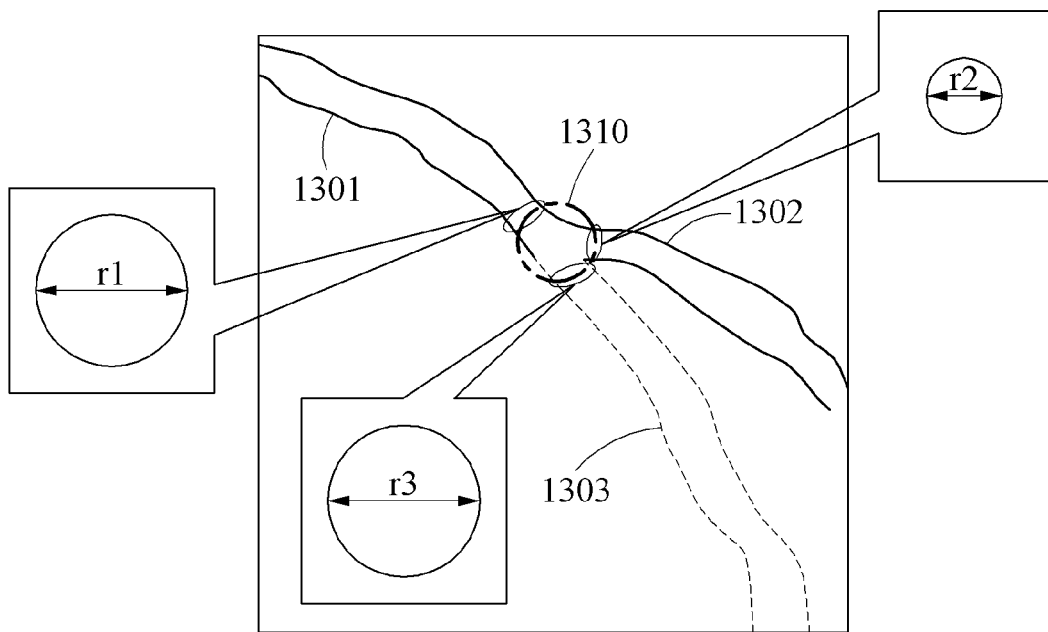
FIG. 13 illustrates a method for identifying and correcting an error in a target blood vessel using diameter information of the target blood vessel.

FIG. 13 illustrates a method for identifying and correcting an error in a target blood vessel using diameter information of the target blood vessel.

According to an example embodiment, the device for processing the blood vessel image may identify and correct a misidentification portion by calculating a diameter difference between the blood vessel branches adjacent to each other in the target blood vessel. For example, the device for processing the blood vessel image may determine branches adjacent to each other as the misidentification portion in response to a case where a diameter difference between the blood vessel branches adjacent to each other in the target blood vessel is a threshold diameter difference or more. The device for processing the blood vessel image may acquire diameter information with respect to each of the blood vessel branches identified based on the branch points. For example, diameters of blood vessel branches 1301, 1302, and 1303 illustrated in FIG. 13 may correspond to r1, r2, and r3, respectively. Illustratively, when the device for processing the blood vessel image first extracts the blood vessel branches 1301 and 1302 as a target blood vessel, the device for processing the blood vessel image may calculate a diameter difference between the blood vessel branches 1301 and 1302. The device for processing the blood vessel image may determine at least one branch of the above-described blood vessel branches 1301 and 1302 as the misidentification portion in the extraction result for the target blood vessel in response to a case where the calculated diameter difference is a threshold diameter difference or more. The blood vessel branches adjacent to each other in the target blood vessel to be actually extracted from the blood vessel image have relatively small diameter difference. Accordingly, there is a possibility that the adjacent blood vessel branches having a diameter difference of the threshold diameter difference or more may be the error portion.

The device for processing the blood vessel image may calculate a diameter difference between the blood vessel branches adjacent to each other with respect to the extracted target blood vessel, but may calculate a diameter difference by smoothing the diameter information of the blood vessel branches. It is general to represent a relatively small change in diameter between the blood vessel branches adjacent to each other in the target blood vessel to be actually extracted from the blood vessel image. However, when the target blood vessel to be extracted includes a blood vessel branch having a disease, a large change in diameter may occur between blood vessel branches adjacent to the blood vessel branch having the disease. Accordingly, the device for processing the blood vessel image may identify a misidentification portion in the extracted target blood vessel by smoothing the diameter information of blood vessel branches by binding the plurality of blood vessel branches to calculate a diameter difference.

The device for processing the blood vessel image may correct the identified error portion in response to a case where the error portion is identified in the target blood vessel using the diameter information. The device for processing the blood vessel image may replace one branch of the branches adjacent to each other with a candidate branch having a diameter difference from the remaining branches of less than the threshold diameter difference, with respect to the identified misidentification portion. Illustratively, when the diameter difference between the blood vessel branch 1301 and the blood vessel branch 1303 which is not extracted as the target blood vessel is less than the threshold diameter difference, the device for processing the blood vessel image may extract the blood vessel branch 1303 instead of the blood vessel branch 1302 as the target blood vessel. The device for processing the blood vessel image may replace the blood vessel branch 1302 with the blood vessel branch 1303 in the extraction result of the target blood vessel. Furthermore, when correcting the identified error portion, the device for processing the blood vessel image may apply a different threshold diameter difference according to a type of blood vessel (e.g., LM, LAD, LCX, and RCA) or a blood vessel area.

Figure 14:
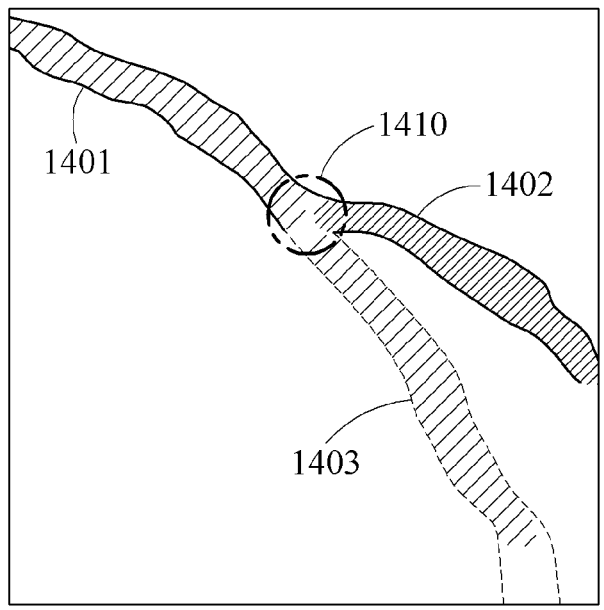
FIG. 14 illustrates a method for identifying and correcting an error in a target blood vessel using brightness information of the target blood vessel.

FIG. 14 illustrates a method for identifying and correcting an error in a target blood vessel using brightness information of the target blood vessel.

According to an example embodiment, the device for processing the blood vessel image may identify and correct a misidentification portion by calculating a brightness difference between blood vessel branches adjacent to each other in the target blood vessel. For example, the device for processing the blood vessel image may determine branches adjacent to each other as the misidentification portion, in response to a case where a brightness difference between the branches adjacent to each other in the target blood vessel is a threshold brightness difference or more. The device for processing the blood vessel image may acquire brightness information with respect to each of the blood vessel branches identified based on the branch points. For example, the brightness of the blood vessel branches may indicate a distribution concentration of a contrast agent injected to obtain a blood vessel image. Illustratively, when the device for processing the blood vessel image first extracts blood vessel branches 1401 and 1402 as a target blood vessel, the device for processing the blood vessel image may calculate a brightness difference between the blood vessel branches 1401 and 1402. The device for processing the blood vessel image may determine at least one branch of the above-described blood vessel branches 1401 and 1402 as the misidentification portion in the extraction result for the target blood vessel in response to a case where the calculated brightness difference is the threshold brightness difference or more. The adjacent blood vessel branches in the target blood vessel to be actually extracted from the blood vessel image have a relatively small change in brightness. Accordingly, there is a possibility that the adjacent blood vessel branches having a brightness difference of the threshold brightness difference or more may be the error portion.

The device for processing the blood vessel image may correct the identified error portion, in response to a case where the error portion is identified in the target blood vessel using the brightness information. The device for processing the blood vessel image may replace one branch of the branches adjacent to each other with a candidate branch having a brightness difference from the remaining branches of less than the threshold brightness difference, with respect to the identified misidentification portion. Illustratively, when the brightness difference between the blood vessel branch 1401 and the blood vessel branch 1403 which is not extracted as the target blood vessel is less than the threshold brightness difference, the device for processing the blood vessel image may extract the blood vessel branch 1403 instead of the blood vessel branch 1402 as the target blood vessel. The device for processing the blood vessel image may replace the blood vessel branch 1402 with the blood vessel branch 1403 in the extraction result of the target blood vessel. Furthermore, when correcting the identified error portion, the device for processing the blood vessel image may apply a different threshold brightness difference according to a type of blood vessel (e.g., LM, LAD, LCX, and RCA) or a blood vessel area. As a result, the device for processing the blood vessel image may perform a preprocessing portion of identifying the error portion of the target blood vessel first extracted by the method of FIGS. 8 to 14, and providing the correction result of the identified error portion to the user.

The device for processing the blood vessel image according to an example embodiment may generate a new extraction result for the target blood vessel based on the model ensemble distinguished from the model ensemble applied in the previous extraction result, in response to a case where the error portion is identified. When the error portion is identified, the device for processing the blood vessel image may generate a new extraction result for the target blood vessel based on one model ensemble distinguished from the model ensemble applied in the previous extraction result among a plurality of stored machine learning models without directly correcting the error portion.

In addition, the device for processing the blood vessel image may generate a plurality of new extraction results for the target blood vessel with respect to each of a plurality of model ensembles on the basis of the model ensembles distinguished from the model ensemble applied in the previous extraction result among the plurality of stored machine learning models. The device for processing the blood vessel image may identify an error portion every extraction result of the target blood vessel generated according to the model ensemble on the basis of at least one of blood vessel structure data related to the target blood vessel, curvature information of the target blood vessel, diameter information of the target blood vessel, and brightness information of the target blood vessel. The device for processing the blood vessel image may automatically select one extraction result closest to the target blood vessel to be actually extracted among generated extraction results for the plurality of target blood vessels as a target blood vessel to provide the selected extraction result to the user. For example, the device for processing the blood vessel image may select an extraction result for a target blood vessel with the smallest identified error portion as the extraction result closest to the target blood vessel to be actually extracted, but is not limited thereto. The device for processing the blood vessel image may extract the selected extraction result as the target blood vessel in response to the selection input of the user. Furthermore, the device for processing the blood vessel image may provide information on the extraction results for the plurality of target blood vessels to the user. The device for processing the blood vessel image may receive one of the extraction results for the plurality of target blood vessels from the user to extract one extraction result indicated by the input as the target blood vessel. Accordingly, the device for processing the blood vessel image may perform a preprocessing process of providing the user with the correction result of the target blood vessel using a different machine learning model.

The device for processing the blood vessel image according to an example embodiment may extract one blood vessel branch of candidate blood vessel branches as the target blood vessel on the basis of a connectivity score for each of the candidate blood vessel branches in response to a case where the error portion is identified in the extraction result of the target blood vessel. When the error portion is identified in the extraction result of the target blood vessel, the device for processing the blood vessel image may select one blood vessel branch of the candidate blood vessel branches capable of correcting the error portion. The device for processing the blood vessel image may calculate a connectivity score for each of the candidate blood vessel branches. The connectivity score is a score indicating the connectivity between a blood vessel branch adjacent to any candidate blood vessel branch and the corresponding candidate blood vessel branch in the extraction result of the target blood vessel. The connectivity score may be calculated on the basis of a degree of matching, a curvature difference, a diameter difference, a brightness difference, etc. for blood vessel structure data between the candidate blood vessel branch and the adjacent blood vessel branch. The connectivity score may correspond to a degree similar to the target blood vessel to be actually extracted from the corrected target blood vessel when the candidate blood vessel branch is included as the target blood vessel.

For example, when the candidate blood vessel branch is extracted as the target blood vessel, the device for processing the blood vessel image may calculate a connectivity score between the candidate blood vessel branch and the blood vessel branches adjacent and connected to the candidate blood vessel branch on the basis of at least one of the blood vessel structure data related to the target blood vessel, the curvature information of the target blood vessel, the diameter information of the target blood vessel, and the brightness information of the target blood vessel. However, the present disclosure is not limited thereto, and the connectivity score for each of the candidate blood vessel branches may be calculated using various methods. The device for processing the blood vessel image may select one blood vessel branch of the candidate blood vessel branches on the basis of the connectivity score. For example, as a blood vessel branch having the highest connectivity score among the candidate blood vessel branches, a blood vessel branch determined to have the smallest error may be selected. The device for processing the blood vessel image may extract the selected blood vessel branch as the target blood vessel.

Illustratively, in FIG. 9, the device for processing the blood vessel image calculates the node connection data 910 to which the first node N1, the third node N3, and the fifth node N5 are connected from the extraction result of the target blood vessel, the device for processing the blood vessel image may determine that the connection between the third node N3 and the fifth node N5 in the node connection data 910 does not match the blood vessel structure data 900. The device for processing the blood vessel image may determine a blood vessel branch corresponding to at least one node of the nodes N3 and N5 corresponding to the connection error as the error portion. When the device for processing the blood vessel image determines the blood vessel branch corresponding to the third node N3 as the error, the device for processing the blood vessel image may exclude the third node N3 which does not match the blood vessel structure data from the node connection data and add the second node N2 matching the blood vessel structure data to the node connection data. In addition, when the device for processing the blood vessel image determines the blood vessel branch corresponding to the fifth node N5 as the error, the device for processing the blood vessel image may exclude the fifth node N5 which does not match the blood vessel structure data from the node connection data and add a sixth node N6 or a seventh node N7 matching the blood vessel structure data to the node connection data. As a result, the device for processing the blood vessel image may calculate a connectivity score for each of candidate blood vessel branches corresponding to the second node, the sixth node, and the seventh node that may be nodes of the target blood vessel. The device for processing the blood vessel image may select a blood vessel branch determined to have the smallest error to extract the selected blood vessel branch as the target blood vessel, on the basis of the connectivity score for each of the candidate blood vessel branches.

As another example, in FIG. 12, when the device for processing the blood vessel image first extracts the blood vessel branches 1201 and 1202 as the target blood vessel, the device for processing the blood vessel image may determine the blood vessel branches as an error portion when a curvature between the blood vessel branches 1201 and 1202 exceeds a threshold curvature. The device for processing the blood vessel image may replace one branch of the branches adjacent to each other with a candidate branch having a curvature with the remaining branches of the threshold curvature or less. Unlike illustrated in FIG. 12, when there is a plurality of candidate blood vessel branches, the device for processing the blood vessel image may calculate a connectivity score for each of the candidate blood vessel branches. The device for processing the blood vessel image may select a blood vessel branch determined to have the smallest error to extract the selected blood vessel branch as the target blood vessel, on the basis of the connectivity score for each of the candidate blood vessel branches. Even in FIGS. 13 and 14, the device for processing the blood vessel image may select and extract one of the candidate blood vessel branches as the target blood vessel in the same manner as described above.

Figure 15:
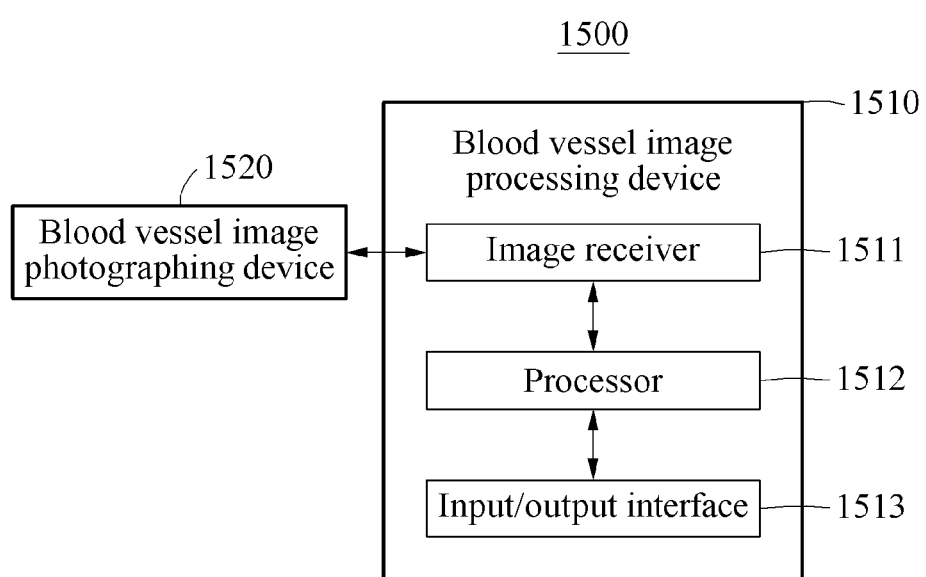
FIG. 15 is a block diagram schematically illustrating a device for processing a blood vessel image according to an example embodiment.

FIG. 15 is a block diagram schematically illustrating a device for processing a blood vessel image according to an example embodiment.

A system 1500 for processing a blood vessel image according to an example embodiment may include a blood vessel image processing device 1510 and a blood vessel image photographing device 1520. The blood vessel image processing device 1510 may include an image receiver 1511, a processor 1512, and an input/output interface 1513.

The image receiver 1511 may receive a blood vessel image photographed by the blood vessel image photographing device 1520. The image receiver 1511 may receive the blood vessel image from the blood vessel image photographing device 1520 through wired/wireless data communication. However, the present disclosure is not limited thereto, and the blood vessel image photographing device 1520 may also be configured to be integrated into the image receiver 1511.

The processor 1512 may extract the target blood vessel from the blood vessel image received from the image receiver using a machine learning model, determine an ROI for the extraction result of the target blood vessel on the basis of the first input received from the user, identify an error portion of the extraction result on the basis of the second input received from the user within the determined ROI, and correct the identified error portion. The operation of the processor 1512 is not limited thereto, and the processor 1512 may perform the operations described above with reference to FIGS. 1 to 14.

The input/output interface 1513 may receive the input from the user to transmit the received input to the processor. For example, the input/output interface 1513 may receive the input according to a mouse operation, a touch operation, and the like. In addition, the input/output interface 1513 may provide visual feedback to the user. For example, the input/ output interface 1513 may output the extraction result of the target blood vessel through the display step by step.

The national R&D projects supporting the present disclosure are as follows.

[Project Unique Number] 1415166912
[Project Number] 20001638
[Ministry name] Ministry of Trade, Industry and Energy-Ministry of Science and Technology Information and Communication-Ministry of Health and Welfare-Ministry of Food and Drug Safety
[Project Management (Special) Institution Name] Korea Evaluation Institute of Industrial Technology
[Research Project Name] Artificial Intelligence Bio-Robot Medical Convergence Project
[Research Subject Name] Development of artificial intelligence assistance and semiautonomous robot system for cardiovascular intervention based on cardiovascular big data
[Managing Department] Seoul Asan Medical Center
[Research Period] May 1, 2018 to Dec. 31, 2020
[Project Unique Number] 1711117085
[Project Number] 2020-0-00159
[Ministry name] Ministry of Science and ICT
[Project Management (Special) Institution Name] Institute for Information & Communication Technology Planning & Evaluation (IITP)
[Research Project Name] Artificial Intelligence Convergence Leading Project
[Research Subject Name] Development of AI-based automated cardiovascular disease diagnosis assistance and surgical tool recommendation system
[Managing Department] Medipixel Co., Ltd.
[Research Period] Apr. 1, 2020 to Dec. 31, 2021
[Project Unique Number] 1425133196
[Project Number] S2758883
[Ministry name] Ministry of SMEs and Startups
[Project Management (Special) Institution Name] Korea Technology & Information Promotion Agency for SMEs
[Research Project Name] Development of Start-up Growth Technology (R&D)
[Research Subject Name] Development of AI-based total occlusion thrombolytic assistance system
[Managing Department] Medipixel Co., Ltd.
[Research Period] Jun. 1, 2019 to May 31, 2020
[Project Unique Number] 1711106903
[Project Number] 2020R1C1C1010470
[Ministry name] Ministry of Science and ICT
[Project Management (Special) Institution Name] National Research Foundation of Korea
[Research Project Name] New Researcher Training Support Project
[Research Subject Name] Development of cardiovascular diagnosis method using deep learning-based intravascular ultrasound image segmentation technology
[Managing Department] University of Ulsan
[Research Period] Mar. 1, 2020 to Feb. 28, 2021

The example embodiments described above may be implemented in hardware components, software components, and/or combinations of hardware components and software components. For example, the device, the method, and the components described in the example embodiments may be implemented using, for example, one or more general-purpose computers or special-purpose computers, such as a processor, a controller, an arithmetic logic unit (ALU), a digital signal processor, a microcomputer, a field programmable gate array (FPGA), a programmable logic unit (PLU), a microprocessor, or other any devices capable of executing and responding instructions. The processing device may perform an operating system OS and one or more software applications performed on the operating system. In addition, the processing device may also access, store, manipulate, process, and generate data in response to execution of software. For convenience of understanding, one processing device may be described to be used, but it can be seen to those skilled in the art that the processing device may include a plurality of processing elements and/or a plurality types of processing elements. For example, the processing device may include a plurality of processors or one processor and one controller. In addition, other processing configurations, such as a parallel processor (parallel processor) are also possible.

Software may include computer programs, codes, instructions, or one or more combinations thereof, and may configure the processing device to operate as desired, or to instruct independently or collectively the processing device. Software and/or data are interpreted by the processing device or may be permanently or temporarily embodied in any type of machines, components, physical devices, virtual equipment, computer storage media or devices, or signal waves to be transmitted, in order to provide commands or data to the processing device. The software may be distributed on a computer system connected via a network, and may be stored or executed in a distributed method. The software and data may be stored in one or more computer readable recording media.

The method according to the example embodiment may be implemented in a form of program instructions which may be performed through various computer means to be recorded in computer readable media. The computer readable medium may include program instructions, data files, data structures, and the like alone or in combination. The program instructions recorded in the medium may be specially designed and configured for the example embodiments or may be publicly known to and used by those skilled in the computer software art. Examples of the computer readable record media include magnetic media, such as a hard disk, a floppy disk, and a magnetic tape, optical media such as a CD-ROM and a DVD, magneto-optical media such as a floptical disk, and hardware devices such as a ROM, a RAM, and a flash memory, which are specially configured to store and execute the program instructions. Examples of the program instructions include high language codes executable by a computer using an interpreter and the like, as well as machine language codes created by a compiler. The hardware devices may be configured to operate as one or more software modules in order to perform the operations of the embodiments, and vice versa.

As described above, although the example embodiments have been described by the restricted drawings, various modifications and variations can be applied on the basis of the example embodiments by those skilled in the art. For example, even if the described techniques are performed in a different order from the described method, and/or components such as a system, a structure, a device, a circuit, and the like described above are coupled or combined in a different form from the described method, or replaced or substituted by other components or equivalents, an appropriate result can be achieved.

The invention claimed is:

1. A method for processing a blood vessel image performed by a processor, comprising the steps of:
    extracting a target blood vessel from a blood vessel image;
    determining a region of interest (ROI) in an extraction result of the target blood vessel on the basis of a first input received from a user;
    identifying a first error portion from the extraction result of the target blood vessel in response to the determining of the ROI and providing the user with a correction result of the first error portion; and
    identifying and correcting a second error portion in the extraction result on the basis of a plurality of points of a second input received from the user in response to a case where the second input is detected from the plurality of points within the ROI where the first error portion is corrected,
    wherein correcting the second error portion on the basis of the plurality of points further comprises:
        determining a blood vessel branch located out of a region corresponding to the movement trajectory of the second input among the blood vessel branches connected with the branch point as a misidentification portion, in response to a case where the point corresponding to the second input moves to a region out of the target blood vessel from the branch point within the region extracted as the target blood vessel; and
        replacing the blood vessel branch with a blood vessel branch indicated by the second input out of the target blood vessel and correcting the remaining extraction result on the basis of the replaced blood vessel branch.

2. The method for processing the blood vessel image of claim 1, wherein
    the determining of the ROI comprises determining a shape of the ROI on the basis of points in which the first input is detected.

3. The method for processing the blood vessel image of claim 1, wherein
    the correcting of the second error portion on the basis of the plurality of points comprises
    detecting whether there is a discontinuity portion in points through which the second input passes, while a point corresponding to the second input moves along a region extracted as the target blood vessel; and
    connecting discontinued portions along a movement trajectory of the second input in response to a case where the discontinuity portion is detected.

4. The method for processing the blood vessel image of claim 1, wherein
    the providing of the user with the correction result of the first error portion further comprises
    providing the user with one or more candidate branches in response to a case where the first error portion is a misidentification portion; and
    replacing a branch corresponding to the first error portion with the selected branch in response to a case of receiving a pointing input for one branch among the one or more candidate branches from the user.

5. The method for processing the blood vessel image of claim 1, wherein
    the providing of the user with the correction result of the first error portion comprises
    connecting a region corresponding to a blood vessel branch corresponding to a start point of a user input and a region corresponding to a blood vessel branch corresponding to an end point of the user input, in response to a case where the user input is detected in a plurality of points with respect to the correction result.

6. The method for processing the blood vessel image of claim 1, wherein
the providing of the user with the correction result of the first error portion comprises
identifying the first error portion on the basis of at least one of blood vessel structure data related to the target blood vessel, curvature information of the target blood vessel, diameter information of the target blood vessel, and brightness information of the target blood vessel, in response to a case where the ROI is determined.

7. The method for processing the blood vessel image of claim 1, wherein
the providing of the user with the correction result of the first error portion comprises
providing the user with the correction result of correcting the first error portion on the basis of at least one of blood vessel structure data related to the target blood vessel, curvature information of the target blood vessel, diameter information of the target blood vessel, and brightness information of the target blood vessel, in response to a case where the error portion is identified.

8. The method for processing the blood vessel image of claim 1, wherein
the providing of the user with the correction result of the first error portion comprises
generating a plurality of new extraction results for the target blood vessel in response to a case where the first error portion is identified; and
selecting one extraction result indicated by the selection input among the plurality of new extraction results in response to the selection input of the user.

9. A device for processing the blood vessel image comprising:
an image receiver for receiving a blood vessel image; and
a processor for extracting a target blood vessel from a blood vessel image, determining a region of interest (ROI) in an extraction result of the target blood vessel on the basis of a first input received from a user, identifying a first error portion from the extraction result of the target blood vessel in response to the determining of the ROI and providing the user with a correction result of the first error portion, and identifying and correcting a second error portion in the extraction result on the basis of (a) a plurality of points of a second input received from the user in response to a case where the second input is detected from the plurality of points within the ROI where the first error portion is corrected, (b) determining a blood vessel branch located out of a region corresponding to the movement trajectory of the second input among the blood vessel branches connected with the branch point as a misidentification portion, in response to a case where the point corresponding to the second input moves to a region out of the target blood vessel from the branch point within the region extracted as the target blood vessel, and (c) replacing the blood vessel branch with a blood vessel branch indicated by the second input out of the target blood vessel and correcting the remaining extraction result on the basis of the replaced blood vessel branch.

* * * * *